US012551393B2

(12) United States Patent
Nahavandi et al.

(10) Patent No.: US 12,551,393 B2
(45) Date of Patent: Feb. 17, 2026

(54) PATIENT SUPPORT APPARATUSES WITH EXIT DETECTION SYSTEMS

(71) Applicant: Stryker Corporation, Kalamazoo, MI (US)

(72) Inventors: Kurosh Nahavandi, Portage, MI (US); Sujay Sukumaran, Portage, MI (US); Marko N. Kostic, Oshawa (CA)

(73) Assignee: Stryker Corporation, Portage, MI (US)

( * ) Notice: Subject to any disclaimer, the term of this patent is extended or adjusted under 35 U.S.C. 154(b) by 851 days.

(21) Appl. No.: 17/280,644

(22) PCT Filed: Nov. 12, 2019

(86) PCT No.: PCT/US2019/060823
§ 371 (c)(1),
(2) Date: Mar. 26, 2021

(87) PCT Pub. No.: WO2020/102129
PCT Pub. Date: May 22, 2020

(65) Prior Publication Data

US 2021/0338505 A1 Nov. 4, 2021

Related U.S. Application Data

(60) Provisional application No. 62/758,795, filed on Nov. 12, 2018.

(51) Int. Cl.
*A61G 7/05* (2006.01)
*A61B 5/00* (2006.01)
*A61B 5/11* (2006.01)

(52) U.S. Cl.
CPC .......... *A61G 7/0524* (2016.11); *A61B 5/1115* (2013.01); *A61B 5/6891* (2013.01);
(Continued)

(58) Field of Classification Search
CPC ..... A61B 5/1115; A61B 5/6891; A61B 5/746; A61B 5/747; A61B 2562/0252;
(Continued)

(56) References Cited

U.S. PATENT DOCUMENTS 5,184,112 A 2/1993 Gusakov
10,260,933 B2 4/2019 Kostic et al.
(Continued)

FOREIGN PATENT DOCUMENTS

WO 2014151577 A1 9/2014

OTHER PUBLICATIONS

European Search Report for International Application No. PCT/US2019/060823 completed Jun. 10, 2022.
(Continued)

*Primary Examiner* — Justin C Mikowski
*Assistant Examiner* — Deborah T Gedeon
(74) *Attorney, Agent, or Firm* — Gardner, Linn, Burkhart & Ondersma LLP

(57) ABSTRACT

A patient support apparatus, such as abed, cot, stretcher, or the like, includes a frame, support surface, exit detection system, and control. The exit detection system includes multiple sensors and a controller configured to issue an exit alert when the patient exits from the support surface. The control is configured to disarm the exit detection system, and the controller is further configured to use outputs from the exit detection sensors to detect when the patient on the support surface may be making an attempt to disarm the exit detection system, and to prevent the patient from disarming the exit detection system during the attempt. The sensors may comprise load cells. In some embodiments, the control is positioned at the foot end of the patient support apparatus, while in other embodiments, the control may be positioned along a siderail of the patient support apparatus.

20 Claims, 9 Drawing Sheets

(52) U.S. Cl.
CPC .............. *A61B 5/746* (2013.01); *A61B 5/747* (2013.01); *A61B 2562/0252* (2013.01); *A61G 2203/30* (2013.01); *A61G 2203/70* (2013.01)

(58) Field of Classification Search
CPC .................. A61B 5/002; A61B 5/6892; A61B 2562/0247; A61G 7/0524; A61G 2203/30; A61G 2203/70; A61G 7/05; A61G 2203/34; A61G 2203/36; A61G 7/0527; A61G 2203/32; A61G 2203/44; A61G 7/00; G08B 25/008; G16H 40/63
USPC ...... 340/573.4, 573.1; 5/611, 428, 600, 607, 5/610, 613, 617, 652, 713
See application file for complete search history.

(56) References Cited

U.S. PATENT DOCUMENTS

| | | | | |
|---|---|---|---|---|
| 10,330,522 | B2 | 6/2019 | Paul et al. | |
| 10,612,963 | B2 | 4/2020 | Paul et al. | |
| 10,716,474 | B2 | 7/2020 | Bodurka et al. | |
| 10,786,408 | B2 | 9/2020 | Sidhu et al. | |
| 10,898,400 | B2 | 1/2021 | Kostic et al. | |
| 2006/0028350 | A1 * | 2/2006 | Bhai | A61B 5/1115 177/144 |
| 2008/0169931 | A1 * | 7/2008 | Gentry | A61B 5/1117 600/300 |
| 2012/0025990 | A1 * | 2/2012 | Tallent | A61B 5/1115 340/573.4 |
| 2014/0210610 | A1 * | 7/2014 | Tatinclaux | A61B 5/1115 340/501 |
| 2014/0333440 | A1 | 11/2014 | Kiani | |
| 2015/0323388 | A1 | 11/2015 | Kostic et al. | |
| 2016/0058641 | A1 | 3/2016 | Moutafis et al. | |
| 2016/0140307 | A1 * | 5/2016 | Brosnan | G06Q 10/10 600/509 |
| 2016/0227022 | A1 * | 8/2016 | Alameh | H03K 17/96 |
| 2017/0098359 | A1 * | 4/2017 | Sidhu | A61G 7/015 |
| 2018/0108239 | A1 | 4/2018 | Pirio et al. | |
| 2018/0293849 | A1 | 10/2018 | Bhimavarapu et al. | |

OTHER PUBLICATIONS

Stryker Patient Care Maintenance Manual Modular Patient System (MPS) 3000 Bed, Mar. 1994.
Stryker Maintenance Manual InTouch Critical Care Bed Model FL27, Sep. 2008.
Stryker Operations Manual MedSurg Bed, Model 3002 S3, Oct. 2010.
CHG Hospital Beds User Manual for "The Spirit Select Bed".
International Application No. PCT/US2019/060823 International Search Report, Apr. 9, 2020.
International Application No. PCT/US2019/060823 Written Opinion of the International Searching Authority, Apr. 9, 2020.

* cited by examiner

PATIENT SUPPORT APPARATUSES WITH EXIT DETECTION SYSTEMS

CROSS-REFERENCE TO RELATED APPLICATIONS

This application claims priority to U.S. provisional patent application Ser. No. 62/758,795 filed Nov. 12, 2018, by inventors Kurosh Nahavandi et al. and entitled PATIENT SUPPORT APPARATUSES WITH EXIT DETECTION SYSTEMS, the complete disclosure of which is incorporated herein by reference.

BACKGROUND

The present disclosure relates to patient support apparatuses, such as beds, cots, stretchers, operating tables, recliners, or the like. More specifically, the present disclosure relates to patient support apparatuses that include sensors for monitoring the motion and/or activity of an occupant of the patient support apparatus and issuing an alert if the occupant is, or may be, about to exit the patient support apparatus.

Existing hospital beds and/or stretchers often include an exit detection system that is adapted to detect when a patient has exited the bed, or when a patient may be about to exit the bed. Typically, such beds include circuitry for providing an audio or visual alarm when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately. The exit detection system itself may be implemented in a variety of manners, including using a plurality of force sensors.

SUMMARY

According to various embodiments, an improved patient support apparatus is provided that includes an exit detection system that resists being disarmed by a patient. In some instances, a patient may resist having an exit alert go off whenever he or she leaves the patient support apparatus, and the patient may therefore seek to disarm the exit detection system via one or more controls on the patient support apparatus. If the patient is successful in disarming the exit detection system, the patient can then exit the patient support apparatus without any alert being generated. Without an alert being generated, caregivers are not notified of the patient's exit and therefore cannot provide assistance to the patient while he or she is out of the patient support apparatus, thereby increasing the possibility of the patient falling and/or injuring himself or herself. According to various aspects discussed in greater detail below, the present disclosure provides improved patient support apparatuses that resist the ability of a patient to exit undetected from a patient support apparatus whose exit detection system has been previously armed.

According to one embodiment of the present disclosure, a patient support apparatus is provided that includes a frame, a support surface, an exit detection system, and a control. The support surface is configured to support a patient thereon. The exit detection system comprises a plurality of exit detection sensors and a controller. The exit detection sensors are configured to detect when a patient exits from the support surface and the controller is configured to issue an exit alert when the patient exits from the support surface. The control is configured to disarm the exit detection system. The controller is further configured to use outputs from the exit detection sensors to detect when the patient on the support surface may be making an attempt to disarm the exit detection system, and to prevent the patient from disarming the exit detection system during the attempt.

According to other aspects of the present disclosure, the exit detection sensors comprise a plurality of load cells configured to detect downward forces exerted on the support surface by the patient. In some embodiments, the controller uses outputs from the plurality of load cells to compute a center of gravity of the patient, and the controller uses the center of gravity of the patient to detect when the patient may be making an attempt to disarm the exit detection system.

In at least one embodiment, the control is positioned at a foot end of the patient support apparatus and the controller determines that the patient may be making an attempt to disarm the exit detection system when a distance between the patient's center of gravity and the foot end of the patient support apparatus decreases below a threshold.

In at least one other embodiment, the control is positioned along a side of the patient support apparatus and the controller determines that the patient may be making an attempt to disarm the exit detection system when a distance between the patient's center of gravity and the side of the patient support apparatus decreases below a threshold.

In some embodiments, the controller prevents the patient from disarming the exit detection system during the attempt by disabling the control.

The controller is further configured, in at least one embodiment, to issue and maintain the exit alert for at least a predetermined minimum amount of time if the controller detects that the patient may be making an attempt to disarm the exit detection system.

In some embodiments, the controller is further configured to use outputs from the exit detection sensors to detect when the patient on the support surface is done making the attempt to disarm the exit detection system, and to enable the control after the patient is done making the attempt.

The controller may be configured to prevent the patient from disarming the exit detection system both before it issues an exit alert and after it has already issued the exit alert, thereby preventing the exit detection system from being disarmed no matter what state (alert or no alert) the exit detection system is currently in.

In some embodiments, the patient support apparatus further comprises a base, a lift subsystem, a plurality of siderails, and a control panel. The lift subsystem is configured to raise and lower the support surface with respect to the base. The plurality of siderails are moveable between raised and lowered positions, and the control panel is positioned on an outside surface of at least one of the siderails and includes the control for disarming the exit detection system.

According to another embodiment of the present disclosure, a patient support apparatus is provided that includes a frame, a support surface, an exit detection system, and a control. The support surface is configured to support a patient thereon. The exit detection system comprises a controller and a plurality of exit detection sensors. The controller uses the exit detection sensors to detect both a patient's position relative to a boundary condition and a distance of the patient from a user interface. The controller is further configured to issue an exit alert when the patient's position crosses the boundary condition. The control is coupled to the user interface and is configured to disarm the exit detection system. The controller is further configured to disable the control when the exit detection system is armed and the distance of the patient from the user interface decreases below a threshold.

In other aspects, the exit detection sensors comprise a plurality of load cells configured to detect downward forces exerted on the support surface by the patient. The controller may use outputs from the plurality of load cells to compute a center of gravity of the patient, and to then use the center of gravity to both detect when the patient's position crosses the boundary condition and when the distance of the patient from the user interface decreases below the threshold.

The control to disarm the exit detection system may be positioned at a foot end of the patient support apparatus, or it may be positioned along a side of the patient support apparatus, or it may be positioned at one or more other locations.

In some embodiments, the controller disables the control for a predetermined minimum amount of time after the distance of the patient from the user interface decreases below the threshold.

The controller may be configured to maintain an exit alert for at least a predetermined minimum amount of time if the controller determines that the distance of the patient from the user interface has decreased below the threshold.

In some embodiments, the patient support apparatus further comprises a second control configured to disarm the exit detection system. The second control is coupled to a second user interface spaced from the user interface, and the controller is further configured to detect a second distance of the patient from the second user interface. The controller disables the second control when the exit detection system is armed and the second distance decreases below a second threshold.

In some embodiments, the threshold and the second threshold are defined such that the patient is able to move to a first location on the support surface where the distance is below the threshold but the second distance is not below the second threshold, and the patient is also able to move to a second location on the support surface where the distance is not below the threshold but the second distance is below the second threshold.

In other aspects, the patient support apparatus further comprises an auxiliary control configured to disarm the exit detection system, and the auxiliary control remains enabled when the exit detection system is armed and the distance of the patient from the user interface decreases below the threshold.

In some embodiments, an access control is also included that is configured to cause, when activated, a particular screen to be displayed on a display of the user interface. In such embodiments, the auxiliary control corresponds to a touch control on the display and the touch control is only shown when the particular screen is displayed on the display. In some embodiments, the particular screen is hidden from view while the exit detection system is armed so that only a knowledgeable user is able to easily access the screen.

According to another embodiment of the present disclosure, a patient support apparatus is provided that includes a frame, a support surface, an exit detection system, and a control. The support surface is configured to support a patient thereon and the exit detection system comprises a controller and a plurality of exit detection sensors. The exit detection sensors are configured to detect both a patient's position relative to a boundary condition and a distance of the patient from a user interface. The controller issues an exit alert when the patient's position crosses the boundary condition. The control is coupled to the user interface and is configured to disarm the exit detection system. The controller issues the exit alert for a first time period if the patient's position crosses the boundary condition and the distance of the patient from the user interface decreases below a threshold. Additionally, the controller issues the exit alert for a second time period if the patient's position crosses the boundary condition and the distance of the patient from the user interface does not decrease below the threshold. The first time period is different from the second time period.

According to other aspects, the first time period is defined to include a minimum amount of time and the second time period does not include a minimum amount of time.

In some embodiments, the second time period is a variable amount of time and the variable amount of time ends when an event occurs. The event may be a user activating the control to disarm the exit detection system, the movement of the patient's position back across the boundary condition, or another event.

In still other embodiments, the first time period is a fixed amount of time and the second time period is a variable amount of time.

The exit detection system may comprise a plurality of load cells configured to detect downward forces exerted on the support surface by the patient. In such embodiments, the controller may be configured to use outputs from the plurality of load cells to compute a center of gravity of the patient, and to use the center of gravity to both detect when the patient's position crosses the boundary condition and when the distance of the patient from the user interface decreases below the threshold.

The controller is configured in some embodiments to disable the control when the exit detection system is armed and the distance of the patient from the user interface decreases below the threshold.

An auxiliary control is included in some embodiments that is configured to disarm the exit detection system, and the auxiliary control remains enabled when the exit detection system is armed and the distance of the patient from the user interface decreases below the threshold. An access control may be included that is configured to cause, when activated, a particular screen to be displayed on a display of the user interface. The auxiliary control corresponds to a touch control on the display that is only shown when the particular screen is displayed on the display.

In some embodiments, both the control and the auxiliary control are positioned at a foot end of the patient support apparatus, while in other embodiments both the control and the auxiliary control are positioned along a side of the patient support apparatus. In still other embodiments, the control and/or auxiliary control are positioned elsewhere.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
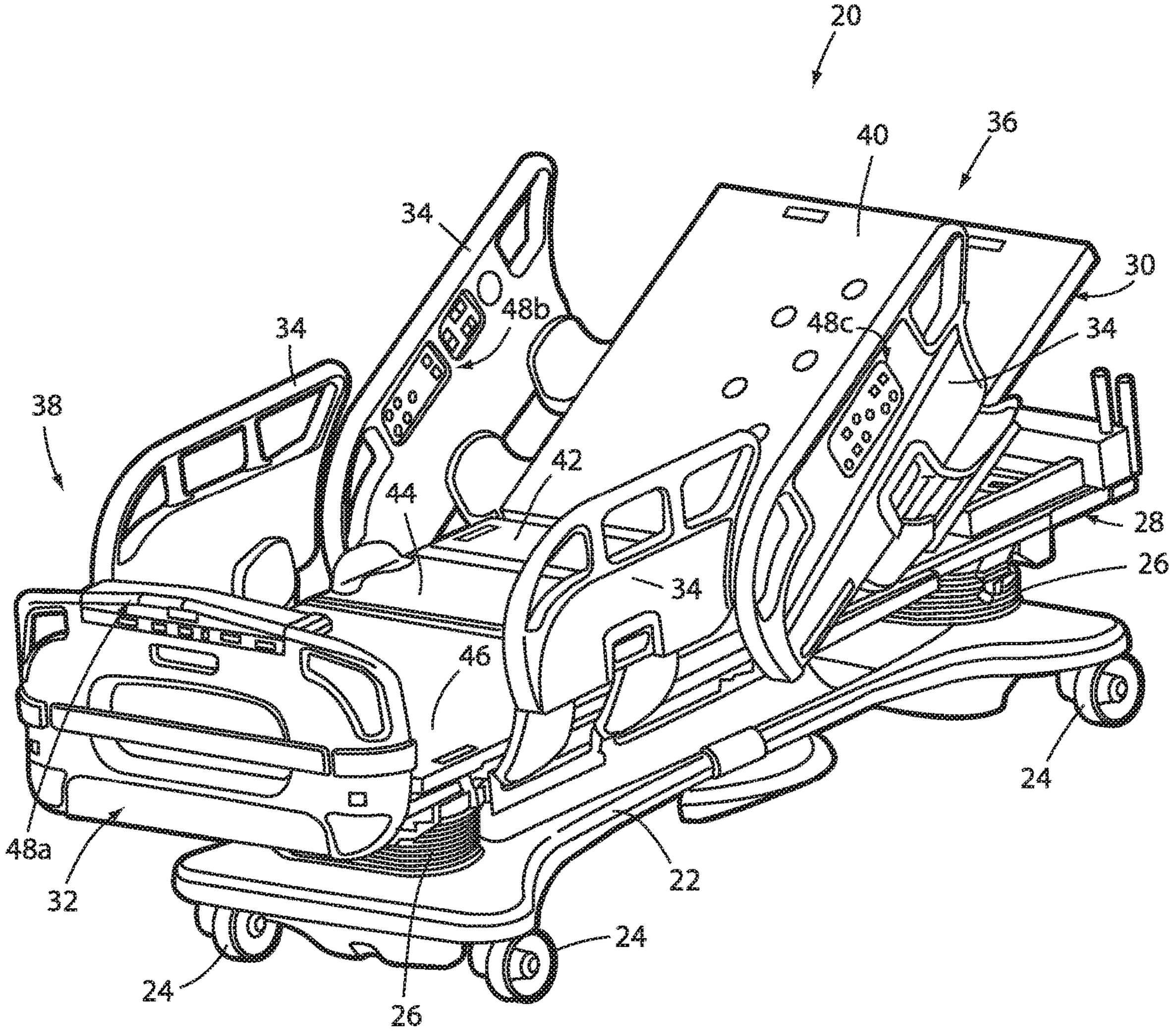
FIG. 1 is a perspective view of a patient support apparatus according to one embodiment of the disclosure.

An illustrative patient support apparatus 20 that may incorporate one or more aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, or any other structure capable of supporting a patient that may be used during times when the patient is not accompanied by a caregiver. For purposes of the following written description, patient support apparatus 20 will be described as a bed with the understanding the following written description applies to these other types of patient support apparatuses.

In general, patient support apparatus 20 includes a base 22 having a plurality of wheels 24, a lift subsystem comprising a pair of lifts 26 supported on the base, a litter frame 28 supported on the lifts 26, and a support deck 30 supported on the litter frame 28. Patient support apparatus 20 further includes a headboard (not shown), a footboard 32, and a plurality of siderails 34. Siderails 34 are all shown in a raised position in FIG. 1 but are each individually movable to a lower position in which ingress into, and egress out of, patient support apparatus 20 is not obstructed by the lowered siderails 34. In some embodiments, siderails 34 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when an occupant lies thereon, his or her head will be positioned adjacent head end 36 and his or her feet will be positioned adjacent foot end 38.

Litter frame 28 provides a structure for supporting support deck 30, the headboard, footboard 32, and siderails 34. Support deck 30 provides a support surface for a mattress (not shown in FIG. 1), or other soft cushion, so that a person may lie and/or sit thereon. Support deck 30 is made of a plurality of sections, some of which are pivotable about generally horizontal pivot axes. In the embodiment shown in FIG. 1, support deck 30 includes a head section 40, a seat section 42, a thigh section 44, and a foot section 46. Head section 40, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 44 and foot section 46 may also be pivotable about generally horizontal pivot axes.

Patient support apparatus 20 further includes a plurality of user interfaces 48 that enable a user of patient support apparatus 20, such as a patient and/or an associated caregiver, to control one or more aspects of patient support apparatus 20. In the embodiment shown in FIG. 1, patient support apparatus 20 includes a footboard user interface **48*a*, a pair of inner siderail user interfaces 48*b* (only one of which is visible), and a pair of outer siderail user interfaces 48*c* (only one of which is visible). Footboard user interface 48*a* and outer siderail user interfaces 48*c* are intended to be used by caregivers, or other authorized personnel, while inner siderail user interfaces 48*b* are intended to be used by the patient associated with patient support apparatus 20. Not all of the user interfaces 48 include the same controls and/or functionality. In the illustrated embodiment, footboard user interface 48*a* includes a substantially complete set of controls for controlling patient support apparatus 20 while user interfaces 48*b* and 48*c* include a selected subset of those controls. As will be discussed in greater detail below, in one embodiment, footboard user interface 48*a* includes an exit detection system disarm control that is not included on either of inner or outer siderail user interfaces 48*b* or 48*c*. In another embodiment discussed more below, one or both of outer siderail user interfaces 48*c* include an exit detection system disarm control that is not present on inner siderail user interfaces 48*b* and that may or may not be included on footboard user interface 48*a***.

In addition to an exit detection system disarm control, user interfaces 48 may include controls for allowing a user to do one or more of the following: change a height of support deck 30, raise or lower head section 40, activate and deactivate a brake for wheels 24, arm the exit detection system, take a weight reading of the patient, activate and deactivate a propulsion system, and communicate with a healthcare facility computer network installed in the healthcare facility in which patient support apparatus 20 is positioned. Inner siderail user interfaces **48*b*** may also include a nurse call control that enables a patient to call a nurse. A speaker and microphone are included in order to allow the patient to aurally communicate with the remotely positioned nurse.

Figure 11:
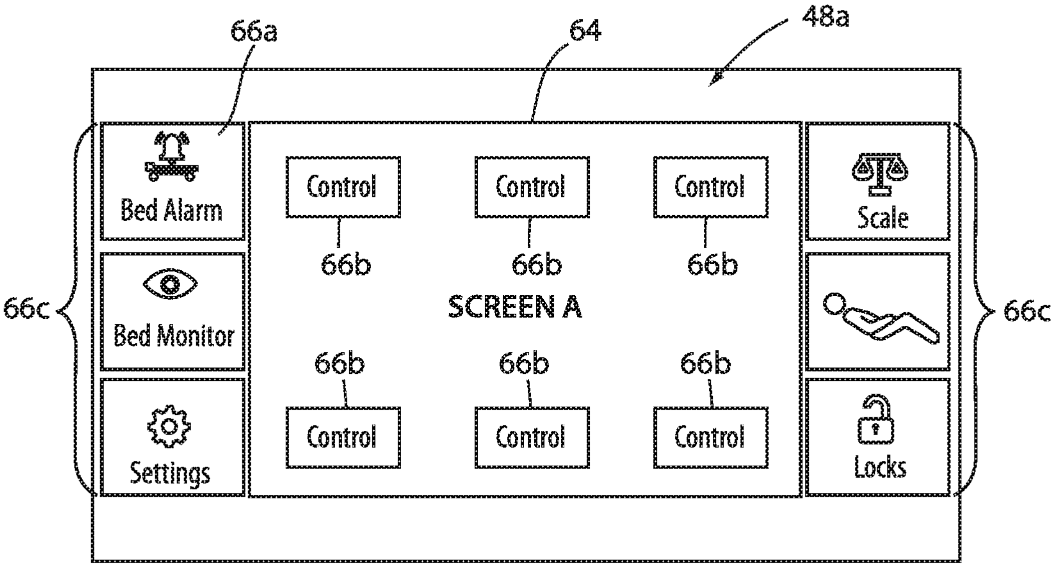
FIG. 11 is a diagram of a user interface of the patient support apparatuses of FIG. 5 or 6 showing an illustrative screen shot that may be displayed during an exit alert.
Figure 12:
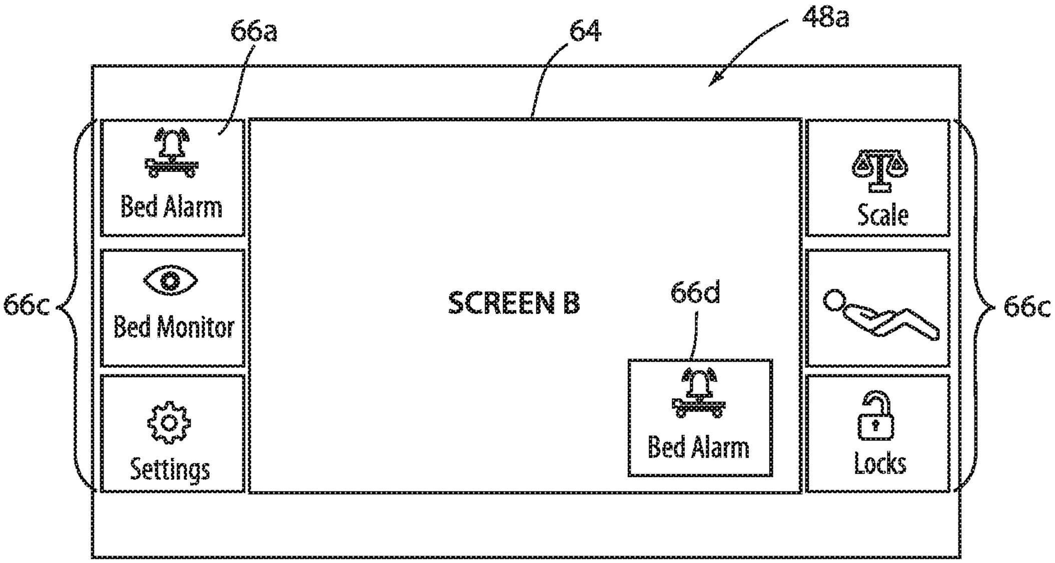
FIG. 12 is a diagram of the user interface of FIG. 11 showing an auxiliary control displayed thereon.

Footboard user interface 48*a* is implemented in the embodiment shown in FIG. 1 as a control panel having a lid (flipped down in FIG. 1) underneath which is positioned a plurality of controls. The controls may be implemented as buttons, dials, switches, or other devices. Any of user interfaces 48*a-c* may also include a display for displaying information regarding patient support apparatus 20. The display may be a touchscreen in some embodiments. An example of one such display is shown in FIGS. 11 and 12 and described in more detail below.

Figure 2:
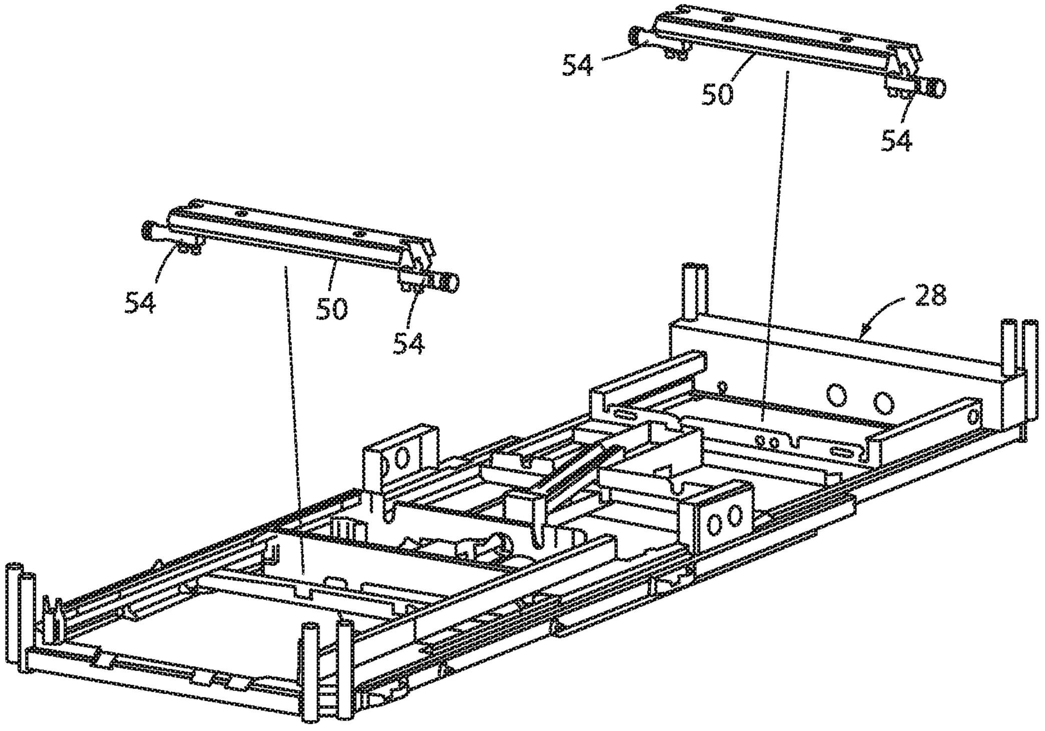
FIG. 2 is a perspective view of a litter frame of the patient support apparatus of FIG. 1.
Figure 3:
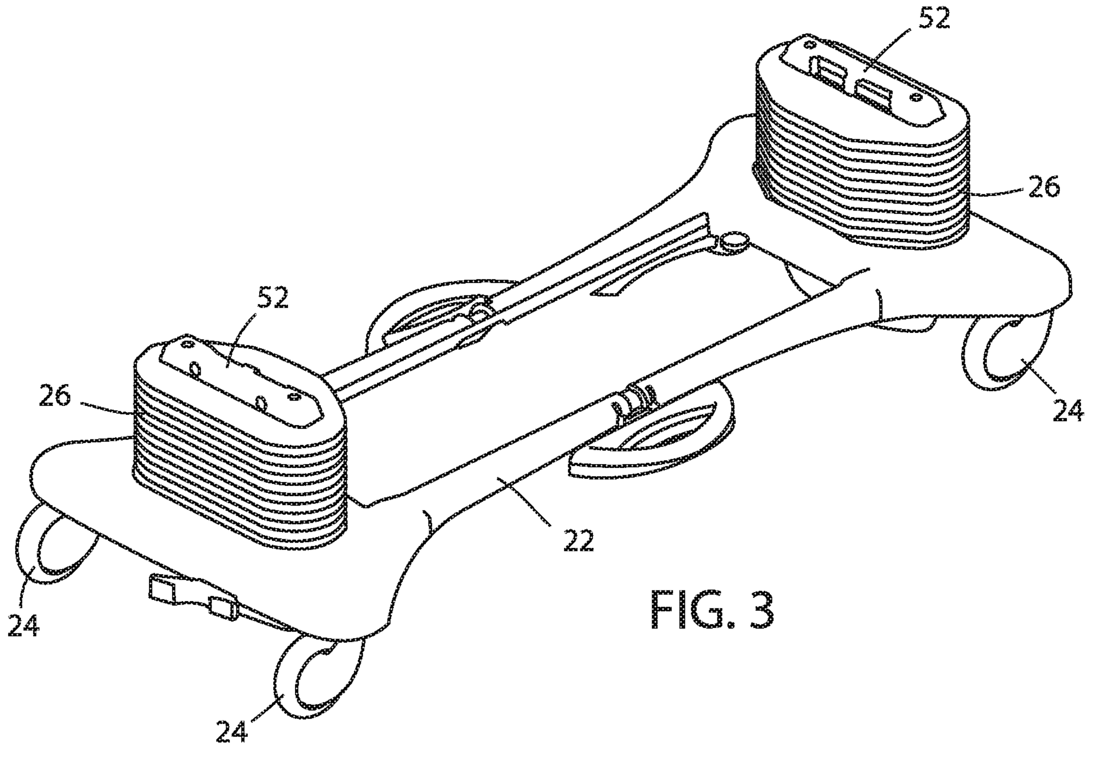
FIG. 3 is a perspective view of a base of the patient support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of load cells 54, which may alternatively be other types of force sensors, such as, but not limited to, linear variable displacement transducers and/or any one or more capacitive, inductive, and/or resistive transducers that are configured to produce a changing output in response to changes in the force exerted against them. Still other types of forces sensors may be used with patient support apparatus 20.

Although the illustrated embodiment of patient support apparatus 20 includes a total of four load cells 54, it will be understood by those skilled in the art that different numbers of load cells 54 may be used in accordance with the principles of the present disclosure. Load cells 54 are configured to support litter frame 28. More specifically, load cells 54 are configured such that they provide complete mechanical support for litter frame 28 and all of the components that are supported on litter frame 28 (e.g. support deck 30, footboard 32, the headboard, siderails 34, etc.). Because of this construction, load cells 54 detect the weight of not only those components of patient support apparatus 20 that are supported by litter frame 28 (including litter frame 28 itself), but also any objects or persons who are wholly or partially being supported by support deck 30. The outputs of load cells 54 are part of an exit detection system 56 (FIG. 4) described in greater detail below.

The mechanical construction of those aspects of patient support apparatus 20 not explicitly described herein may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that those aspects of patient support apparatus 20 not explicitly described herein can alternatively be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of those aspects of patient support apparatus 20 not explicitly described herein may also take on forms different from what is disclosed in the aforementioned references.

Figure 4:
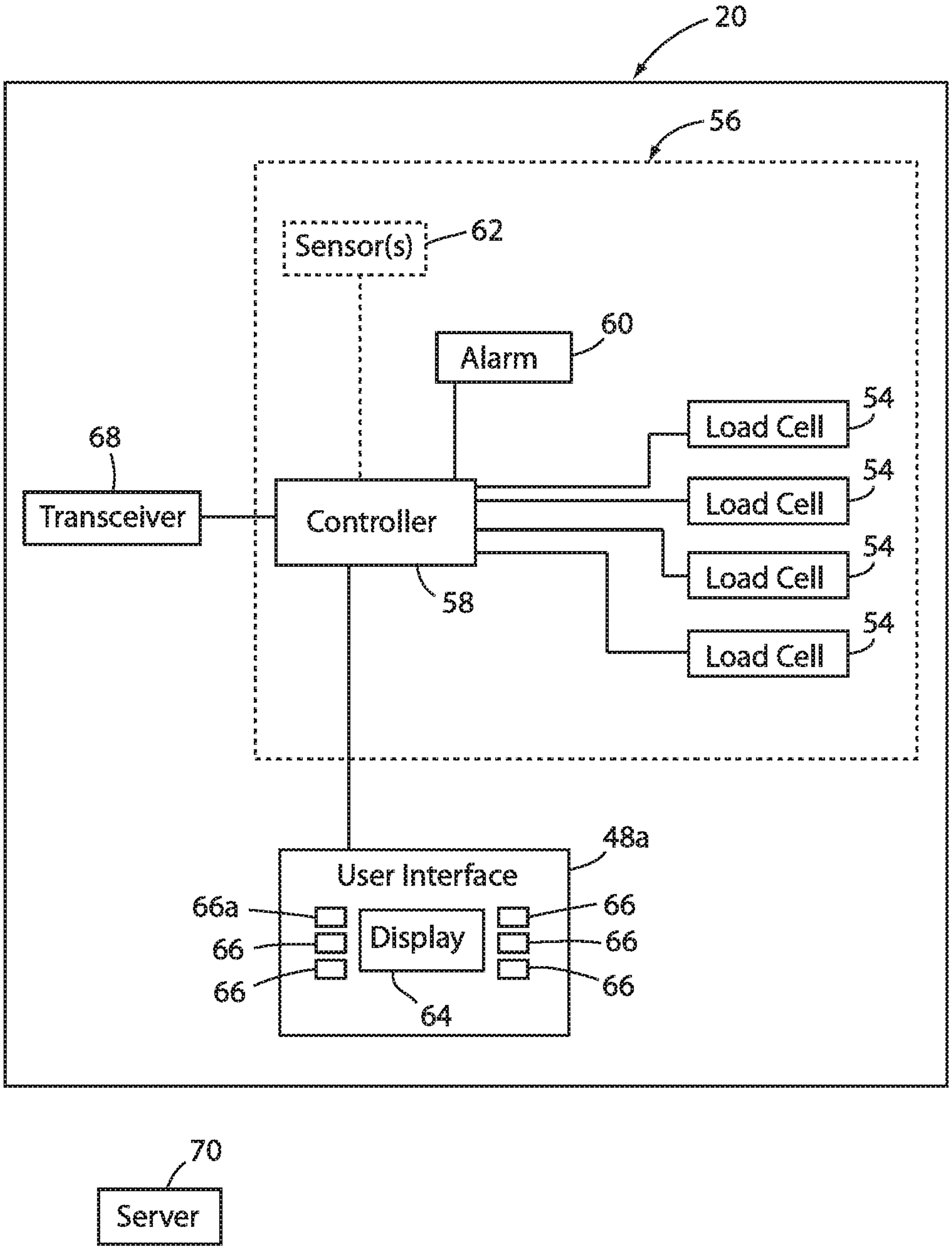
FIG. 4 is a diagram of a control system of the patient support apparatus of FIG. 1.

As shown more clearly in FIG. 4, patient support apparatus 20 includes an exit detection system 56 that is adapted to determine when an occupant, such as, but not limited to, a patient, of patient support apparatus 20 is moving and is likely to exit patient support apparatus 20. The particular structural details of exit detection system 56 can vary widely. In the embodiment shown in FIG. 4, exit detection system 56 includes load cells 54, a controller 58, an alarm 60, and one or more sensors 62. In other embodiments, exit detection system 56 may include other components in addition to those shown in FIG. 4. In general, it will be understood by those skilled in the art that exit detection system 56 may be modified in a variety of ways to omit one or more of the components shown in FIG. 4, add one or more additional components thereto, and/or substitute other components for one or more of the components shown in FIG. 4. Some of these various embodiments are discussed in greater detail below.

Sensors 62 are an optional component that, as discussed further below, may be omitted in some embodiments of exit detection system 56. When included, sensors 62 may include one or more of a variety of different sensors that are useful in helping exit detection system 56 to more accurately and/or more quickly determine when a patient may be about to exit from patient support apparatus 20. Such sensors 62 may include sensors for detecting the position of one or more siderails 34, one or more vital signs of the patient supported on patient support apparatus 20, one or more sensors for detecting the height of the patient, and/or other sensors. Further explanation of these and other types of sensors 62 that may be used with exit detection system 56 are disclosed in more detail in commonly assigned U.S. patent application Ser. No. 15/266,575 filed Sep. 15, 2016, by Anuj K. Sidhu et al. and entitled PERSON SUPPORT APPARATUSES WITH EXIT DETECTION SYSTEMS, the complete disclosure of which is incorporated herein by reference.

Load cells 54 are adapted to detect downward forces exerted by an occupant of support deck 30. Thus, when an occupant is positioned on support deck 30 and substantially still (i.e. not moving in a manner involving accelerations that cause forces to be exerted against support deck 30), load cells 54 will detect the weight of the occupant (as well as the weight of any components of patient support apparatus 20 that are supported—directly or indirectly—by load cells 54). Load cells 54 may therefore be used as a scale subsystem in addition to their role in exit detection system 56.

In at least one embodiment of exit detection system 56, the outputs from load cells 54 are processed by controller 58 to determine a center of gravity of the occupant, as will be discussed in greater detail below, in order to determine if the occupant is about to exit patient support apparatus 20. In alternative embodiments, the outputs from load cells 54 are analyzed, not to determine a center of gravity, but instead to determine a weight distribution and/or a change in weight distribution, such as by determining one or more ratios of the relative weights sensed by the load cells 54 and using them to determine if the occupant is about to exit patient support apparatus 20. In still other embodiments, load cells 54 may be modified to detect forces other than, or in addition to, the downward forces exerted by the occupant, such as, but not limited to, one or more forces in a transverse direction. Other types of sensors may also or alternatively be used for determining the occupant's weight.

Controller 58 is constructed of any electrical component, or group of electrical components, that are capable of carrying out the functions described herein. In many embodiments, controller 58 is a conventional microcontroller, although not all such embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in a memory (not labeled) accessible to controller 58.

Controller 58 is in communication with footboard user interface 48*a*, as shown in FIG. 4. Controller 58 also communicates with the user interfaces 48*b* and 48*c* that are positioned on patient support apparatus 20, although these are not shown in FIG. 4 for purposes of clarity. Footboard user interface 48*a* includes a display 64 and a plurality of controls 66. Display 64 is a touch screen display in at least some embodiments, although it will be understood that a non-touch screen display 64 may alternatively be used. It will also be understood that footboard user interface 48*a* may be implemented without any display at all. Controls 66 are shown in FIG. 4 as touch sensitive controls that may be physically implemented in a variety of different manners. In some embodiments, controls 66 are implemented as capacitive sensors positioned adjacent display 64 that capacitively detect when a user presses them. In other embodiments, controls 66 are implemented as buttons, switches, or other types of force or touch-sensitive devices. In still other embodiments, one or more of controls 66 may be incorporated into touchscreen display 64 (see, e.g. FIGS. 8, 9, 11 & 12). Still other variations are possible.

Footboard user interface 48*a* includes a disarm control 66*a* that is adapted to disarm exit detection system 56 when it is activated (e.g. pressed). Disarm control 66*a* is shown in FIG. 4 as a particular control separate from display 64, but it will be understood that disarm control 66*a* may be configured as a graphic, icon, or other control that is displayed on display 64 and activated when touched (i.e. when display 64 is implemented as a touchscreen, disarm control 66*a* may be accessed via the touchscreen display 64, rather than a control that is physically separate from display 64). It will also be understood that disarm control 66*a* may be a control that serves other functions. For example, in some embodiments of patient support apparatus 20, disarm control 66*a* may be a toggle control that, when activated, switches between arming and disarming exit detection system 56 (e.g. it arms exit detection system 56 if exit detection system 56 is not currently armed, and disarms exit detection system 56 if exit detection system 56 is currently armed). In still other embodiments, disarm control 66*a* may be a context sensitive control whose function depends upon the content of information currently being displayed on display screen 64, and/or the state of user interface 48*a*. That is, disarm control 66*a* may be used to control other functions in addition to the disarming of exit detection system 56, depending upon the information being displayed on display 64 or depending upon other parameters (e.g. whether exit detection system 56 is armed or not). In any event, when disarm control 66*a* is activated to disarm exit detection system 56, the disarming turns off exit detection system 56 so that an alert is not issued when the patient exits from patient support apparatus 20 or otherwise moves outside of a permissible zone of movement, as discussed in more detail below.

In the illustrated embodiment, when exit detection system 56 is armed, controller 58 receives the outputs from load cells 54 and processes them to determine a center of gravity of the patient. One method of computing the patient's center of gravity from the output of load cells 54 is described in more detail in commonly assigned U.S. Pat. No. 5,276,432 issued to Travis and entitled PATIENT EXIT DETECTION MECHANISM FOR HOSPITAL BED, the complete disclosure of which is incorporated herein by reference. Other methods may be used.

After computing the center of gravity, controller 58 determines if the location of the center of gravity is within an acceptable boundary or not. If it is, controller 58 does nothing until a next set of readings from load cells. If it is not, controller 58 issues an exit alert using alarm 60 and/or a remotely positioned alarm (or, in some embodiments, waits until a predetermined number of successive center or gravity readings are outside of the boundary in order to avoid alerting on the basis of transients). When issuing a remote alert, controller 58 utilizes a transceiver 68 to transmit the alert to a remote alarm. Transceiver 68 may be a wireless transceiver (e.g. Wi-Fi, Bluetooth, ZigBee, etc.) or it may be a wired transceiver (e.g. Ethernet). In other embodiments, transceiver 68 may be a wired nurse-call interface adapted to communicate with a nurse call system. One example of such a wired nurse-call interface is the cable interface disclosed in more detail in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference. The remote alert may be sent to a remote server, such as server 70, a nurses' station, and/or other locations. One or more of user interfaces 48*a-c* may include one or more controls to enable a user to choose whether to issue such alerts locally, remotely, or both. Still other aspects of the exit alert may be user-configurable using one or more of the user interfaces 48.

Figure 5:
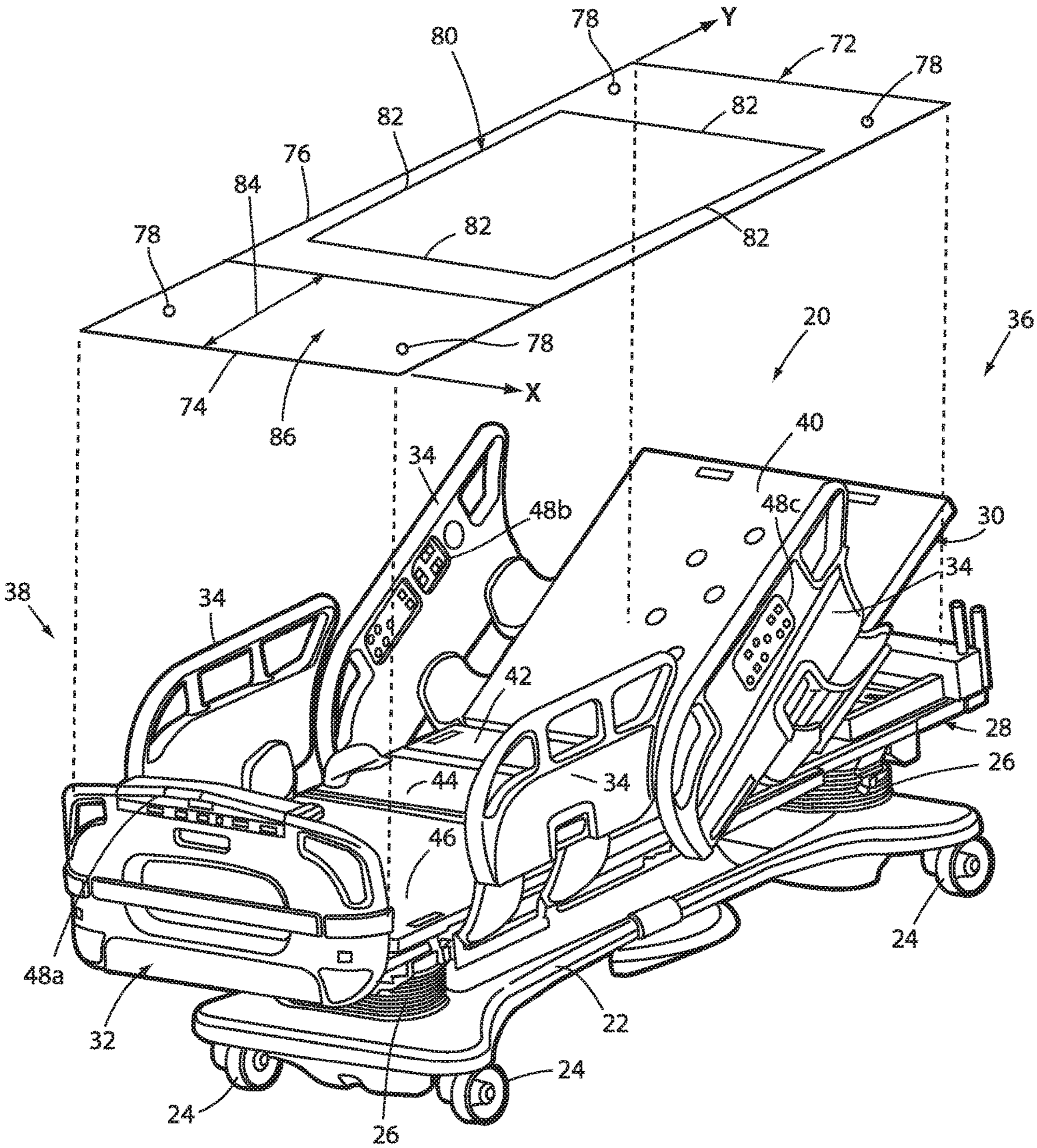
FIG. 5 is a diagram of the patient support apparatus of FIG. 1 showing an imaginary plane with a first illustrative set of zones in which patient movement triggers one or more actions.

FIG. 5 shows in more detail one manner in which exit detection system 56 is configured to operate. FIG. 5 shows a planar coordinate frame of reference 72 positioned above patient support apparatus 20. Frame of reference 72 is shown positioned above patient support apparatus 20 in FIG. 5 for purposes of clarify. In actuality, frame of reference 72 is more easily understood as being positioned in a plane common to the generally horizontal plane of litter frame 28, although the vertical position of frame of reference 72 with respect to litter frame 28 is not important. Frame of reference 72 is shown to have an X-axis 74 that vertically aligns with a foot end edge of litter frame 28 and a Y-axis 76 that vertically aligns with a right edge (from the perspective of a patient lying on his or her back on support deck 30) of litter frame 28 of patient support apparatus 20. The alignment of the axes 74, 76 with these edges of litter frame 28 is not important so long as the location and orientation of litter frame 28 within frame of reference 72 is known.

The location of load cells 54 within frame of reference 72 is also known and stored in a memory accessible to controller 58. These locations are shown in FIG. 5 and identified with the reference number 78. A permissible zone of movement 80 is also shown in FIG. 5. Zone of movement 80 is shown in FIG. 5 to be generally rectangular shaped with four boundaries 82. It will be understood that the particular size and shape of zone of movement 80 shown in FIG. 5 is merely one illustrative example of zone 80, and that zone 80 may be modified to include different shapes or sizes, including, but not limited to shapes having non-straight edges. In some embodiments of patient support apparatus 20, the user is able to select between different sizes and/or shaped zones 80 when arming exit detection system 56. By selecting different sizes and/or shapes of zone 80, the user is able to configure exit detection system 56 to permit different levels of acceptable movement before an exit alert is issued. In this manner, the user is able to select whether a caregiver is to be alerted when the patient moves a little, moves a lot, fully exits from patient support apparatus 20, partially exits, etc.

As indicated, zone 80 defines the permissible range of movement of a patient such that, as long as the patient's center of gravity, as calculated within frame of reference 72, remains within the boundaries 82 of zone 80, controller 58 will not issue an exit alert. In some embodiments, controller 58 is configured to automatically change one or more of the boundaries of zone 80, in addition to allowing a user to change the boundaries of zone 80. That is, in addition to allowing a user to select how much movement to permit a patient before issuing an alert, controller 58 is configured in some embodiments to automatically change the shape and/or size of the user-selected zone based on one or more factors that influence the likelihood, or unlikelihood, of the patient exiting patient support apparatus 20. Such factors include, but are not limited to, one or more of the following: (a) the weight of the occupant; (b) the height of the occupant; (c) a ratio of the occupant's height and weight; (d) the gender of the occupant; (e) a fall risk assessment of the occupant; (f) values of one or more vital signs of the occupant; (g) a position of the siderails 34; (h) a downward force being applied to one or more of the siderails 34; (i) a position or orientation of one or more other components of patient support apparatus 20; (j) the environment or surroundings in which patient support apparatus 20 is positioned; (k) a proximity of a caregiver to patient support apparatus 20; (l) a time of day; (m) one or more medical conditions of the occupant; (n) a body orientation of the occupant; (o) a current height of litter frame 28, (p) a width of support deck 30 (for those embodiments of patient support apparatus 20 having an adjustable width deck 30); (q) a length of support deck 30 (for those embodiments of patient support apparatus 20 having an adjustable length deck 30); (r), a length of time since the patient last exited, etc. These and other factors that may be used by controller 58 to make automatic adjustments to the size and/or shape of a selected zone 80 are disclosed and described in more detail in commonly assigned U.S. patent application Ser. No. 15/266,575 filed Sep. 15, 2016, by inventors Anuj K. Sidhu et al. and entitled PERSON SUPPORT APPARATUSES WITH EXIT DETECTION SYSTEMS, the complete disclosure of which is incorporated herein by reference.

In addition to determining whether the patient's center of gravity has moved outside of the boundaries 82 of zone 80, controller 58 is configured to also determine if the patient's center of gravity has approached within a threshold distance 84 of footboard user interface **48*a*. That is, controller 58 determines if the users center of gravity has moved into a disablement zone 86 where the edge of disablement zone 86 farthest from footboard user interface 48*a* is defined by threshold distance 84. If the patient's center of gravity has moved into disablement zone 86, controller 58 is configured to disable disarm control 66*a*. That is, controller 58 is configured to prevent a person, including the patient, from disarming exit detection system 56 using disarm control 66*a* whenever the patient's center of gravity is determined to lie within disablement zone 86. This prevents the patient from disarming exit detection system 56 using disarm control 66*a*. The disablement may last for a predetermined amount of time or it may last until the patient moves out of the disablement zone 86**, or it may last for a different period of time.

In some instances, patients who are left in patient support apparatuses 20 with exit detection system 56 activated are desirous of leaving patient support apparatus 20 without causing an exit alert to issue. Such patients may not want to trouble the healthcare staff, may believe they are fully capable of exiting the patient support apparatus 20 without assistance, or may have other reasons to want to exit without notifying healthcare personnel. Such patients may learn that the exit detection system can be disarmed by activating disarm control **66*a*. In order to prevent such patients from disarming exit detection system 56 and exiting from patient support apparatus 20 undetected, controller 58 is configured to prevent exit detection system 56 from being disarmed by the patient. That is, whenever the patient moves too close (e.g. within threshold distance 84) to the user interface 48*a*, controller 58 disables disarm control 66*a*, thereby making disarm control 66*a* inoperative. If the user presses on disarm control 66*a*, or otherwise tries to activate it, while it has been disabled by controller 58, nothing happens. That is, exit detection system 56** is not disarmed.

Threshold distance 84 and disablement zone 86 are shown in FIG. 5 as being positioned toward foot end 38 of patient support apparatus 20. This is because, in that particular embodiment, disarm control **66*a* is positioned on footboard user interface 48*a*, which is likewise positioned at foot end 38 of patient support apparatus 20. If disarm control 66*a* were to be positioned at a different location on patient support apparatus 20, disablement zone 86 would be positioned elsewhere on patient support apparatus 20 and the line indicating threshold distance 84 would likewise be positioned and/or oriented in a manner different from what is depicted in FIG. 5. More specifically, if disarm control 66*a* were positioned somewhere other than on footboard 32, disablement zone 86 would be repositioned to a location that was near the disarm control 66*a* so that the disarm control 66*a* could be disabled if the patient attempted to use it to disarm exit detection system 56. An example of such a changed location is illustrated in FIG. 6**.

Figure 6:
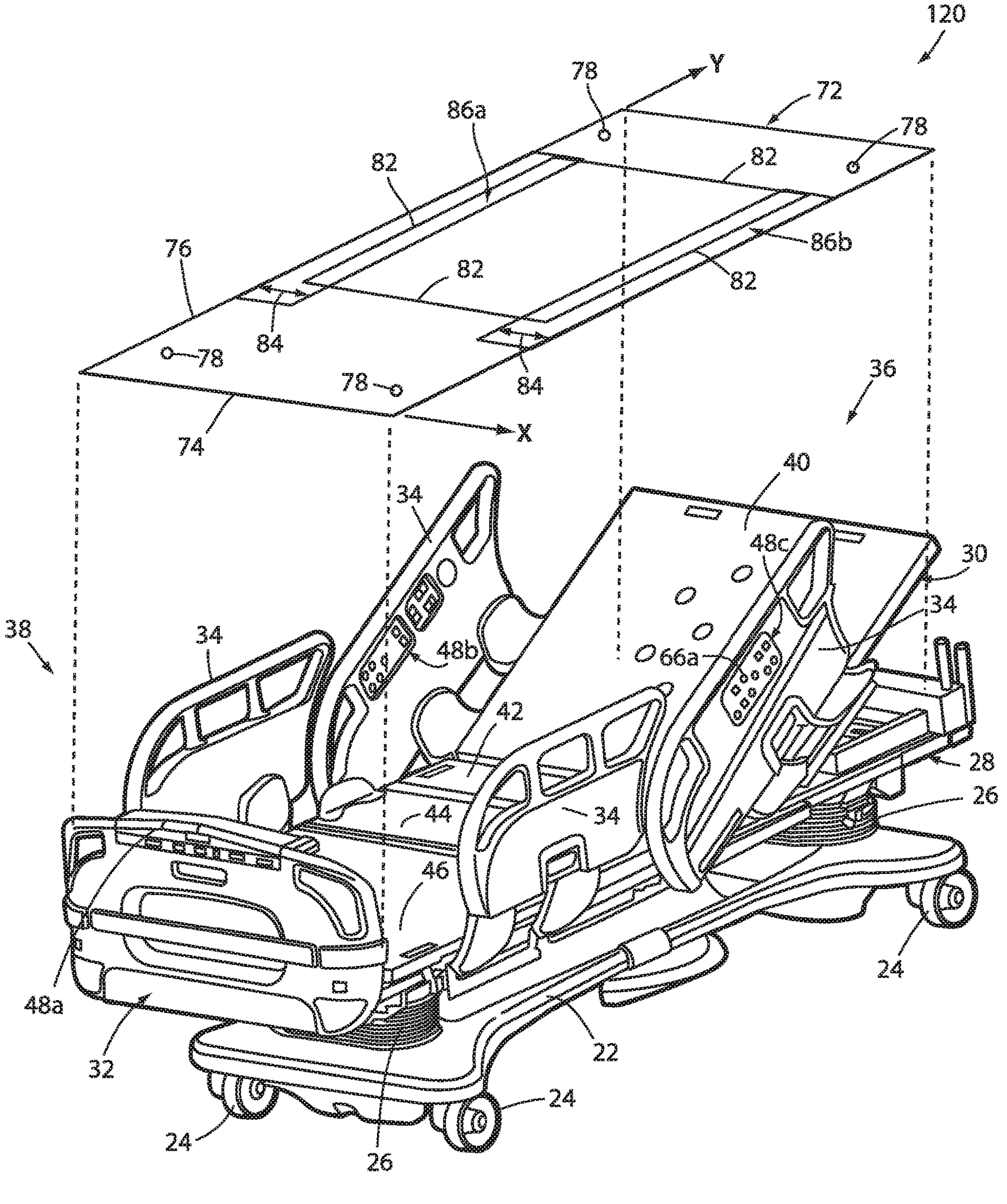
FIG. 6 is a diagram of a modified patient support apparatus showing an imaginary plane with a second set of zones in which patient movement triggers one or more actions.

FIG. 6 provides an illustration of a modified patient support apparatus 120 in which disarm control **66*a* is not positioned on footboard 32. Instead, patient support apparatus 120 includes a first disarm control 66*a* positioned on a first one of the siderails 34, a second disarm control 66*a* positioned on a second one of the siderails 34, and no disarm control positioned on footboard user interface 48*a*. In some modified embodiments of patient support apparatus 120, footboard user interface 48*a* is completely eliminated, although not in the embodiment depicted in FIG. 6. The two disarm controls 66*a* of patient support apparatus 120 are positioned on siderails that are located on opposite sides of patient support apparatus 120. In some embodiments, these disarm controls 66*a* may be positioned on the siderails at locations that are separated from the respective siderail user interfaces 48*c*, but in the illustrated embodiment, disarm controls 66*a* are both positioned within their respective user interfaces 48*c***.

Patient support apparatus 120 also differs from patient support apparatus 20 in that controller 58 of patient support apparatus 120 is programmed to include two disablement zones 86*a* and 86*b*, rather than a single disablement zone. Each disablement zone 86*a*, 86*b* corresponds to a respective disarm control 66*a*. That is, the first disablement zone 86*a* is positioned within frame of reference 72 at a location that is adjacent to the location of the first of the siderails 34 having a disarm control 66*a*, and the second disablement zone 86*b* is positioned within frame of reference 72 at a location that is adjacent to the location of the second of the siderails 34 having the disarm control 66*a*. In this manner, if a patient on patient support apparatus 20 moves sufficiently close to either of the siderails 34 on which a disarm control 66*a* is located, controller 58 disables those disarm controls 66*a*.

In some embodiments, controller 58 is programmed to disable both disarm controls 66*a* whenever a patient's center of gravity moves within one of disablement zones 86*a*, 86*b*. In other embodiments, controller 58 is programmed to disable only the disarm control 66*a* located closest to the disablement zone 86 in which the patient's center of gravity is currently located. In still other embodiments, patient support apparatus 20 or 120 is modified to include a disarm control 66*a* on footboard user interface 48*a* and one on each of the outside siderail user interfaces 48*c*. In such a modified embodiment, controller 58 may be programmed to disable all three disarm controls 66*a* whenever the patient's center of gravity moves into one of the three disablement zones 86, or it may be programmed to only disable the disarm control 66*a* closest to the disablement zone 86 in which the patient's center of gravity is currently located.

It will be understood by those skilled in the art that the size, shape, and position of the disablement zones 86 shown in FIGS. 5 and 6 are merely illustrative examples of suitable disablement zones 86. In either embodiment, distance threshold 84 might be modified to be a curved or other type of non-straight line. It will also be understood that disablement zones 86 may extend further in either the X or Y direction of frame of reference 72 than the outer edges of litter frame 28. For example, in the example of FIG. 5, disablement zone 86 is shown terminating on its right and left sides at the edges of litter frame 28. Disablement zone 86 could, however, be extended beyond these edges so that a patient who leaned over the edge of patient support apparatus 20, or who partially exited along a side of patient support apparatus 20, would not be able to disarm exit detection system 56 using disarm control 66*a*.

It will also be understood by those skilled in the art that the size, shape, and position of the one or more disablement zones 86 are independent from the size, shape, and/or position of the zone(s) of permitted movement 80. That is, the boundaries of disablement zones 86 may or may not overlap with any one or more of the boundaries of permitted movement zones 80. As a result, in some embodiments—depending upon the position, size, and shape of the zones 80 and 86, controller 58 may disable disarm control 66*a* only after it has issued an exit alert, while in other embodiments controller 58 may disable disarm control 66*a* before an exit alert is issued. It may also be possible in the same embodiment to have controller 58 disable disarm control 66*a* before an exit alert is issued in some situations, and in other situations to disable disarm control 66*a* after an exit alert is issued, depending upon the particular location of the patient's center of gravity at the moment it triggered the alert and crossed into a disablement zone 86.

It bears noting that controller 58'*s* disablement of disarm control 66*a* whenever a patient's center of gravity moves into a disablement zone 86 does not disable any of the other controls on that same user interface 48. It also bears noting that, in those embodiments of patient support apparatus 20 wherein one or more of disarm controls 66*a* are multi-function controls, controller 58 may be configured to not disable the other function(s) which are controlled by disarm control 66*a*. Thus, for example, if disarm control 66*a* also functions to enable a user to navigate to different control screens and/or menus on display 64, controller 58 may be programmed to continue to allow a user to use disarm control 66*a* to navigate to the different control screens and/or menus on display 64. Alternatively, if display 64 is a touchscreen and disarm control 66*a* is activated by touching the touchscreen, controller 58's disablement of disarm control 66*a* does not require disabling all functions performed utilizing the touch screen 64—just the disarming function.

Figure 7:
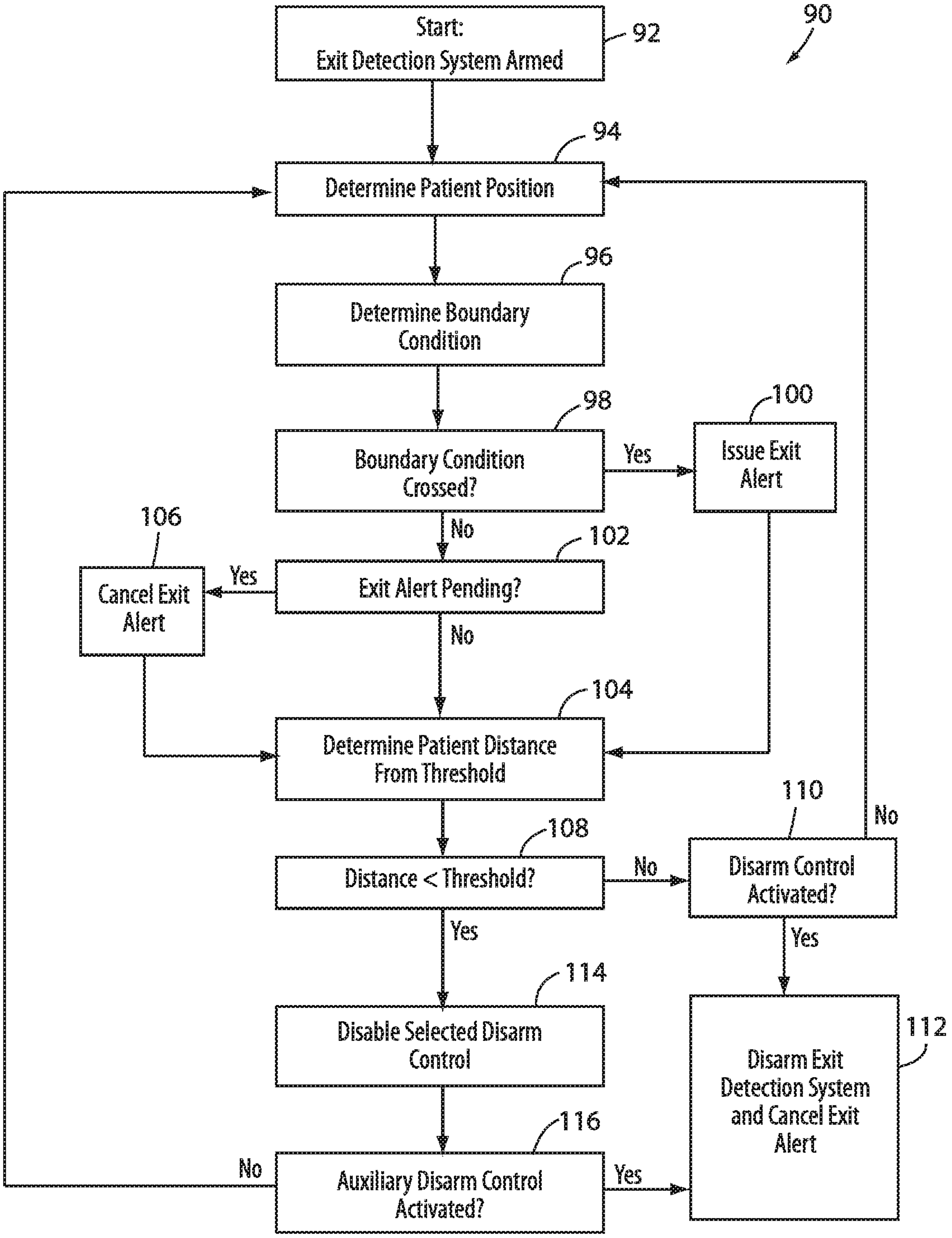
FIG. 7 is diagram of a first exit alerting algorithm that may be implemented by the patient support apparatuses of FIG. 5 or 6.

FIG. 7 illustrates in greater detail a first exit alerting algorithm 90 that may be executed by controller 58 of patient support apparatus 20, 120, or another patient support apparatus having an exit detection system 56 and one or more disarm controls 66*a*. Exit alerting algorithm 90 begins at step 92 where a user arms the exit detection system 56 using an appropriate control 66 located on one or more of the user interfaces 48. After exit detection system 56 is armed, controller 58 proceeds to step 94 where it determines the patient's position on patient support apparatus 20. In the illustrated embodiment, the patient's position is determined by calculating the patient's center of gravity, which is done based upon readings from the load cells 54 and the known location of load cells 54 in frame of reference 72. As noted previously, however, controller 58 may be programmed in other embodiments to determine the patient's position in a different manner.

After determining the patient's position at step 94, controller 58 proceeds to step 96 where it determines the appropriate boundary condition. This boundary condition refers to the boundaries 82 of permitted zone of movement 80. As noted previously, patient support apparatus 20 is configured in some embodiments to allow a user to select different sized and/or shaped zones 80. Further, as was also discussed previously, patient support apparatus 20 is configured in some embodiments to have controller 58 automatically adjust one or more of the size and/or shape of zone 80 based upon one or more dynamic factors, such as any of those discussed previously (e.g. siderail status, patient vital signs, etc.). In those cases where patient support apparatus 20 neither allows a user to select from multiple zones 80 nor makes automatic adjustments to the size or shape of the zone 80, controller 58 performs step 96 by retrieving from an accessible memory the data that defines the boundaries 82 of zone 80 in frame of reference 72.

After determining the appropriate boundaries 82 of zone 80, controller 58 proceeds to step 98 where it determines whether the patient has crossed one or more of the boundaries 82 determined at step 96. In the illustrated embodiment, this involves determining whether the patient's current center of gravity (determined at step 94) is within permitted zone of movement 80 or outside of zone 80. If it is outside of zone of movement 80, controller 58 moves to step 100 and issues an alert. (Alternatively, as mentioned previously, controller 58 may require multiple, successive readings of the patient's center of gravity being outside of zone 80 before issuing an alert in order to avoid issuing an alert on the basis of a transient reading from one or more of the load cells 54).

If controller 58 determines at step 98 that the patient's center of gravity is within permitted zone of movement 80, then it moves to step 102. At step 102, controller 58 determines whether an exit alert is currently being issued or not. When controller 58 executes algorithm 90 and reaches step 102 for the first time, the answer to this inquiry will always be no, and controller 58 will therefore proceed to step 104. However, when controller 58 performs step 102 for the second time, or any subsequent time thereafter, an exit alert may be currently issuing. In such a case, controller 58 moves to step 106 and cancels the alert. After canceling the alert at step 106, controller 58 moves to step 104.

Steps 98, 102, and 106 serve to allow a patient to shut off an existing exit alert by moving back to a location within permitted zone of movement 80. Patient support apparatus 20 may be configured in other manners for shutting off an exit alert. In some embodiments, patient support apparatus 20 is configured such that an exit alert cannot be shut off by simply having the patient move back to within permitted zone 80. In such embodiments, algorithm 90 is modified to remove steps 102 and 106 and one or more alternative or additional steps may be added in order to implement the exit alert shut off function.

At step 104, controller 58 determines how far the patient's position (e.g. center of gravity) is away from the one or more user interfaces 48 having the disarm control 66*a*. In some embodiments, this may involve determining the distance between the patient's center of gravity and a point, or cluster of points, (not shown) in frame of reference 72 corresponding to the specific location of the user interface 48 having the disarm control 66*a*. In other embodiments, such as the ones shown in FIGS. 5 and 6, this involves determining the distance between the patient's center of gravity and the edge of the litter frame closest to the user interface(s) 48 having the disarm control 66*a*. In still other embodiments, other measurements of the proximity of the patient's center of gravity to the user interface 48 having the disarm control 66*a* may be used.

After completing step 104, controller 58 moves to step 108 where it determines whether the distance determined at step 104 is less than threshold distance 84. In other words, controller 58 determines at step 108 whether or not the patient's current center of gravity lies within the disablement zone 86 (or one of the disablement zones 86, if there are multiple). If controller 58 concludes that the patient's center of gravity lies outside of the disablement zone 86, controller 58 moves to step 110. At step 110, controller 58 determines if the user has activated disarm control 66*a* or not. If so, controller 58 responds by disarming exit detection system 56 at step 112. If not, controller 58 returns to step 94 where it takes a fresh set of readings from load cells 54, makes a new determination of the patient's current location, and proceeds through exit alerting algorithm 90 in the manner previously described.

Step 110 allows a user to disarm exit detection system 56 if the patient's current center of gravity does not lie within any of the disablement zones 86. Further, the disarming of exit detection system 56 at step 112 also terminates any existing exit alerts. Thus, for example, if a patient moves outside of a permitted zone of movement 80 at step 98 and an exit alert is issued at step 100, one way of canceling this alert is to activate the disarm control 66*a*, provided the patient's center of gravity is not inside a disablement zone 86. This can be done, for example, by a caregiver who is positioned in the room, or by another individual who is in the room. Of course, if the patient's center of gravity is located in a disablement zone 86, then an existing exit alert cannot be cancelled via disarm control 66*a* because, from step 108, controller 58 proceeds to step 114, rather than to step 110, which bypasses disarm control step 110.

At step 114, controller 58 disables the disarm control 66*a*. In those embodiments of patient support apparatus 20 or 120 that have more than one disarm control 66*a*, controller 58 disables only the one closest to the patient's current center of gravity (although controller 58 can be modified to disable the other controls 66*a* as well, if desired). By disabling the disarm control 66*a* at step 114, neither the patient nor anyone else who is positioned in the room will be able to disarm the exit detection system 56 using disarm control 66*a* until the patient moves out of a disablement zone 86. This prevents the patient from circumventing the alerting function of the exit detection system 56.

Figure 8:
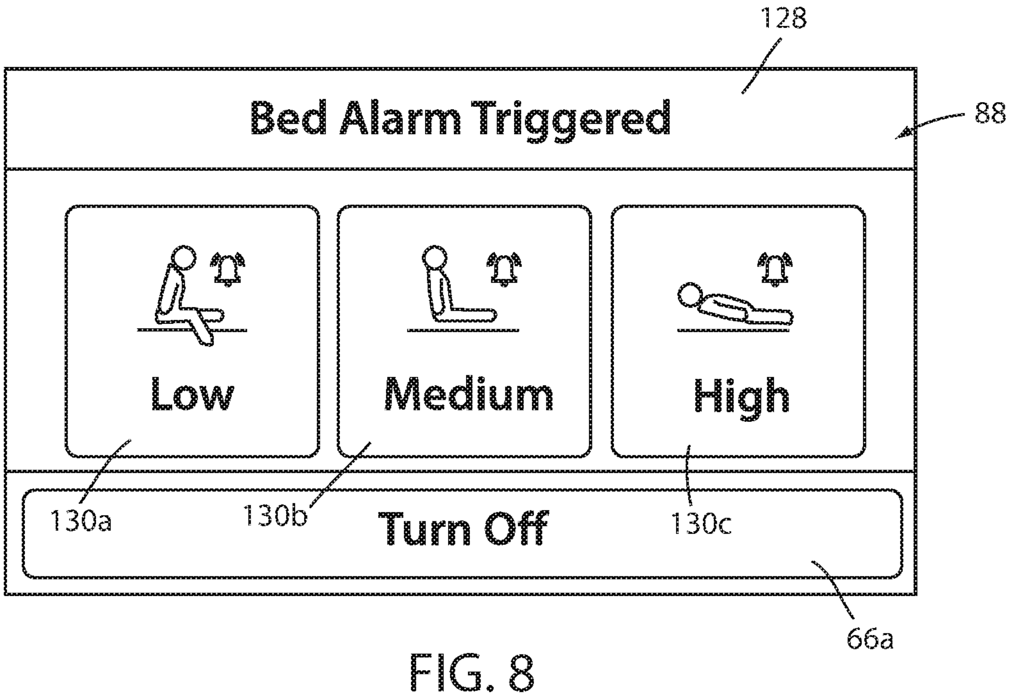
FIG. 8 is a screen shot from a display of the patient support apparatus of FIG. 1 showing an example of a screen that may be displayed in response to an exit detection alert being issued.
Figure 9:
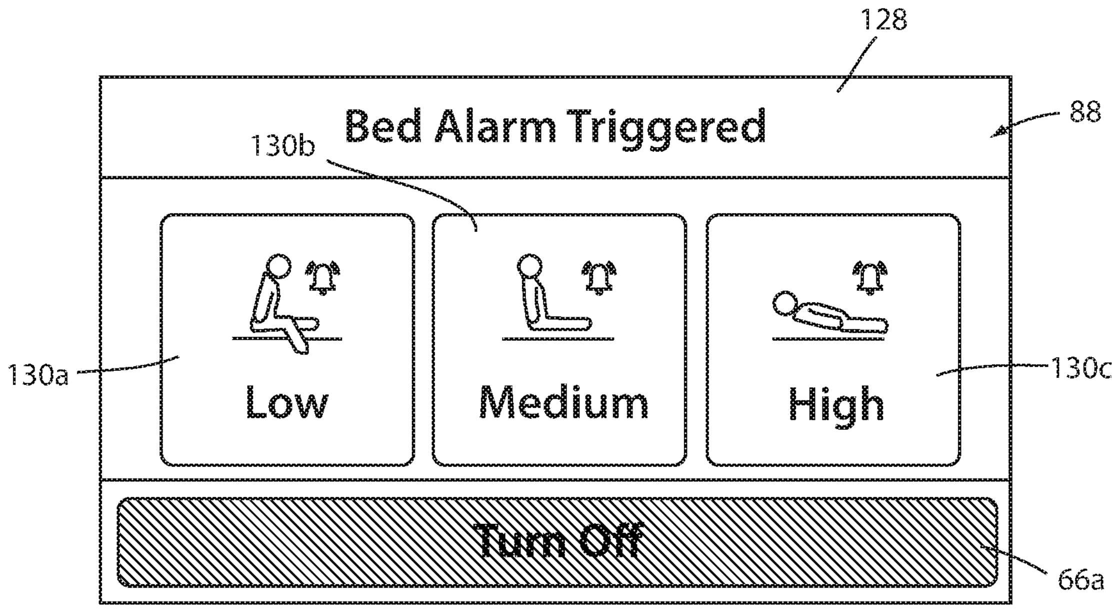
FIG. 9 is a screen shot from the display of the patient support apparatus of FIG. 1 showing an example of how the screen shown in FIG. 8 is changed when a patient's position is detected within a disablement zone.

FIGS. 8-9 depict one illustrative manner in which controller 58 implements step 114. It will be understood that this only one of a large variety of different ways in which controller 58 may disable disarm controls 66*a*. FIG. 8 shows a screen shot 88 of an illustrative example of a screen displayable on display 64 when controller 58 detects an exit condition and issues as exit alert at step 100. As can be seen in FIG. 8, screen shot 88 includes an alert indicator 128 indicating that a patient exit has been detected. Screen shot 88 further includes a plurality of zone selectors 130*a, b*, and *c*. Zone selectors are adapted to allow a user to select the size and/or shape of zone of movement 80. That is, by selecting one of selectors 130*a*-*c*, the user can change the definition of boundaries 82. In the example shown in FIG. 8, there are three different zones of movement 80 that are selectable. A first one, which is the smallest, and therefore sets off an exit alert with the least amount of patient movement, is selected by a user by pressing selector 130*a*. A second one, which is larger, and therefore allows more movement of a patient before setting off an alert, is selected by a user by pressing selector 130*b*. A third one, which is the largest of all of them and allows the most patient movement before an alert is issued, is selected by a user by pressing selector 130*c*. As can be seen in FIG. 8, the user had previously selected the medium sized zone, as indicated by selector 130*b* being highlighted.

Screen shot 88 further includes an example of a disarm control 66*a*. After the exit detection system has been activated, disarm control 66*a* can be pressed by a user to disarm the exit detection system. However, when controller 58 detects at step 108 (FIG. 7) that a user has moved within the threshold distance, it proceeds to step 114, as described previously, and disables the disarm control 66*a*. An example of this is illustrated in FIG. 9, which shows the same screen shot 88 of FIG. 8, but modified by having disable control 66*a* presented in a non-operative fashion. Specifically, in this example, disable control 66*a* of FIG. 9 has been ghosted, and controller 66 thus does not disable exit detection system 56 if a user presses on disable control 66*a* when it is in this ghosted state. This ghosted state can be terminated in algorithm 90 by having the patient move back outside of the disablement zone 86 or by activating an auxiliary disarm control, as discussed below.

In some situations, it may be desirable to allow the exit detection system 56 to be disarmed without requiring the patient to move out of disablement zone 86. This is particularly true if a caregiver is present in the room and is ready to assist the patient out of patient support apparatus. Rather than forcing the patient to move out of disablement zone 86 in order to disarm exit detection system 56 (or rather than continuing to listen to an audible exit alarm while the patient is out of patient support apparatus 20), patient support apparatus 20 and/or 120 can be configured to include an auxiliary disarm control for disarming exit detection system 56 (see, e.g. auxiliary disarm control 66*d* of FIG. 12). The auxiliary disarm control, unlike disarm control 66*a*, is not disabled when the patient moves into disablement zone 86, but instead remains enabled regardless of the patient's position. The auxiliary disarm control is designed such that it is generally not apparent to a patient, but is known to caregivers. This enables a caregiver to disarm exit detection system 56 while a patient is in a disablement zone 86, but substantially prevents a patient from circumventing the alerting function of exit detection system 56 (e.g. getting out of patient support apparatus 20 undetected after a caregiver has armed exit detection system 56).

The auxiliary control may take on a variety of different forms, but is generally difficult for a patient to discover. Indeed, in some embodiments, the auxiliary disarm control is configured such that a patient will likely not be able to activate it even after witnessing the caregiver utilizing it. In some embodiments, the auxiliary disarm control requires the caregiver to proceed through one or more button presses, or other steps. In other embodiments, the auxiliary disarm control may be an unmarked control, may require pressing and holding one or more controls for a lengthier time than a typical button press, may require a specific sequence or combination of button presses or other actions, may require detecting the nearby presence of a caregiver-worn badge (e.g. an RF ID tag), or may involve a combination of one or more of these actions. In any of these configurations, the point is that the patient is unlikely to know how to, or be able to, activate this auxiliary disarm control.

It will be understood by those skilled in the art that the auxiliary disarm control is one of several optional features that, in some embodiments, is omitted from patient support apparatus 20, 120. If it is omitted, controller 58 proceeds from step 114 directly back to step 94. If it is included, controller 58 checks at step 116 to see if the auxiliary disarm control has been activated. If it has, controller 58 proceeds to step 112, where it disarms exit detection system 56 and cancels any existing exit alert. If the auxiliary disarm control is not activated at step 116, controller 58 returns to step 94 where it re-determines the patient's position based on a fresh set of readings from load cells 54. Controller 58 then follows through exit alerting algorithm 90 in the manner previously described.

As an alternative to the auxiliary disarm control (or an addition, in some embodiments), patient support apparatus 20 and/or 120 may be configured to disable the disarm control at step 114 for only a limited amount of time. The precise amount of time that controller 58 disables disarm control 66*a* for at step 114 may vary from embodiment to embodiment. In one embodiment, it is on the order of 5-15 seconds. By limiting the amount of time the disarm control 66*a* is disabled for, there is typically no need for an auxiliary disarm control because, if a caregiver is nearby and wishes to cease the audio and/or visual effects of an existing exit alarm, he or she can simply wait for the time period to expire and then utilize disarm control 66*a* to disarm the exit detection system. Although disabling the disarm control 66*a* for only a limited amount of time allows a patient to shut off the exit detection system 56 after the time period has expired, this is generally not a concern for two reasons: first, the movement necessary by the patient to activate the disarm control 66*a* will typically trigger an alarm from the exit detection system 56, and second, this alarm will trigger for a long enough period of time such that it will likely not be overlooked by caregivers (in contrast to some existing patient support apparatuses that can allow a patient to shut off the exit alarm within a second or two, which can be quick enough for caregivers to overlook, in some situations).

Figure 10:
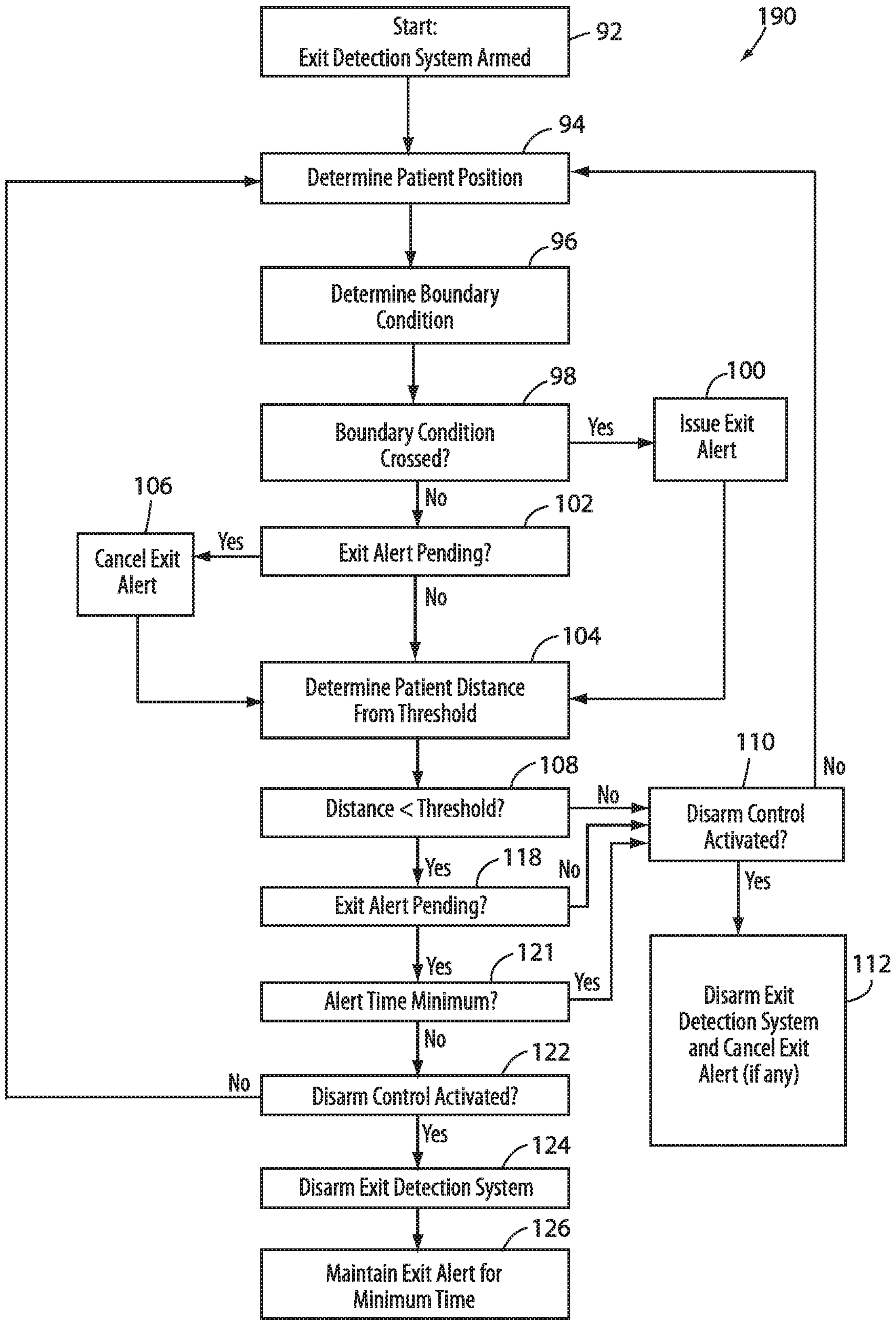
FIG. 10 is a diagram of a second, alternative exit alerting algorithm that may be implemented by the patient support apparatuses of FIG. 5 or 6.

FIG. 10 illustrates an alternative exit alerting algorithm 190 that may be implemented by controller 58 of patient support apparatus 20 or 120, or another patient support apparatus. Exit alerting algorithm 190 differs from exit alerting algorithm 90 primarily in that it does not disable any disarm controls 66*a*, yet still functions to substantially prevent a patient from exiting from patient support apparatus 20 undetected (i.e. exiting after a caregiver armed exit detection system 56 but without issuing an alert). As will be discussed more below, exit alerting algorithm 190 accomplishes this by ensuring that issued exit alerts last for sufficient duration to be noticed and appropriately addressed by the healthcare staff.

Exit alerting algorithm 190 includes a number of steps that are the same as corresponding steps of exit alerting algorithm 90. Those same steps are provided with the same reference number and operate in the same manner previously described. These same steps includes start step 92, patient position determination step 94, boundary condition determination step 96, boundary crossing determination step 98, exit alert issuance step 100, existing alert check step 102, existing alarm cancellation step 106, distance determination step 104, threshold crossing determination step 108, disarm step 110, and termination step 112. Exit alerting algorithm 190 differs from exit alerting algorithm 90 starting at step 121. If controller 58 determines at step 108 that the distance of the patient's center of gravity away from the user interface 48 with a disarm control 66*a* is less than the threshold 84, controller 58 proceeds to step 118.

At step 118, controller 58 determines if an exit alert is currently pending (which would have been issued at step 100). If no exit alert is issued, controller 58 proceeds to step 110 where it allows a user to disable exit detection system 56, if desired. If not desired, controller 58 returns to step 94 from step 110 and proceeds in the manner previously described. If an exit alert is currently pending at step 118, controller 58 proceeds to step 121, where it determines for how long the exit alert has been pending. More specifically, controller 58 determines at step 121 whether the issued exit alert has been pending for a predetermined minimum amount of time. As will be discussed more, the predetermined minimum amount of time is a time period that is generally considered long enough to notify appropriate healthcare providers that an exit alert has issued and should be responded to. In some embodiments, the predetermined time period may be on the order of one or more minutes, although other time periods may be used.

Controller 58 executes step 121 by keeping track of when an exit alert has issued and monitoring the time that has passed since then. Thus, when controller 58 issues an exit alert at step 100, it marks the time at which this exit alert was issued, starts a timer, or otherwise keeps track of the amount of time that passes from the moment the alert is issued. Controller 58 then compares this time measurement to the predetermined minimum at step 121. If the exit alert has been pending for more than the predetermined minimum, controller 58 proceeds to step 110 and allows the user to disarm exit detection system 56, if desired. If the exit alert has not been pending for the predetermined minimum amount of time, controller 58 proceeds from step 121 to step 122. At step 122, controller 58 determines if the disarm control 66*a* has been activated. If it has not, controller 58 returns back to step 94 and proceeds in the manner previously described.

If a person has activated a disarm control 66*a* at step 122, controller 58 proceeds to disarm the exit detection system 56 at step 124, but maintains the exit alert for the minimum amount of time at step 126. After the minimum amount of time has passed, controller 58 terminates the exit alert and exit alert algorithm 190 terminates. The difference between step 112 and steps 124 and 126 is that when controller 58 disarms exit detection system 56 at step 112, it also immediately terminates any existing exit alerts. In contrast, when controller 58 disarms exit detection system 56 at step 124, it does not terminate the existing exit alert immediately, but instead waits until the minimum amount of time has passed and then terminates the exit alert (step 126)

Exit alerting algorithm 190 therefore does not disable disarm control 66*a*, but it does ensure that, if a patient sets off an exit alert and moves too close to a disarm control 66*a* (i.e. within a disablement zone 86), the patient cannot silence the exit alert until a minimum amount of time has passed. This prevents the situation that is possible in some prior art patient support apparatuses where a patient, after setting off an exit alert, moves quickly to disarm the exit detection system such that the alert lasts for a time period so short that is does not cause the appropriate personnel to respond to it.

One result of exit alerting algorithm 190 is that exit alerts are issued by exit detection system 56 for potentially two different time periods, depending upon whether the patient moves into a disablement zone 86 or not. If he or she triggers an exit alert but does not move into a disablement zone 86, exit detection system 56 will maintain the exit alert until it is disarmed or the patient moves back into a zone of permitted movement 80 (or, in some embodiments, a fixed amount of time has transpired—which may be the same as, or different from, the minimum time period of steps 121 and 126). If he or she triggers an exit alert and moves into a disablement zone 86, the exit alert will last for at least the predetermined minimum amount of time (e.g. the time used in steps 121 and 126). In this case, it is also possible for the length of the exit alert to extend beyond the predetermined amount of time. For example, if, after expiry of the predetermined time period, the patient has still not moved back into a permitted zone and no one has yet activated the disarm control 66*a*, exit detection system 56 will continue to issue the exit alert beyond the predetermined time period. On the other hand, if the patient has moved back into a zone 80 or the disarm control 66*a* has been activated, exit detection system 56 will shut off the alert when the predetermined minimum time period has elapsed. One or both of the time periods used by exit detection system 56 for issuing an exit alert may therefore both be fixed, both be variable, or some combination thereof.

FIGS. 11 and 12 illustrate in more detail one manner in which user interface 48*a* (or another user interface 48 on patient support apparatus 20, 120) may be implemented. In addition, FIGS. 11 and 12 illustrate one manner of implementing an auxiliary disarm control 66*d* utilizing a touchscreen for display 64. As noted previously, auxiliary disarm control 66*d*, unlike disarm control 66*a*, is not disabled when the patient moves into a disablement zone 86. User interface 48*a* includes a plurality of touchscreen controls 66*b* that are displayed on a screen A (FIG. 11) and a plurality of non-touchscreen controls 66*c* that are positioned adjacent to touchscreen display 64. Disarm control 66*a*, in this particular embodiments, is one of the non-touchscreen controls 66*c*, although it will be understood that in different embodiments, disarm control 66*a* could be implemented as a touchscreen control 66*b* (see, e.g. FIGS. 8-9). The touchscreen controls 66*b* may perform a variety of different functions, and the number, function, layout, size, and/or other characteristics of these controls may vary from what is shown in FIG. 11, and may also vary depending upon what screen is being displayed at a given time by display 64. Touchscreen controls 66*b* may, for example, control movement of patient support apparatus 20, change one or more settings, take weight readings, etc.

At least one of touchscreen controls 66*b* is an access control that, when activated, brings up screen B on display 64 (FIG. 12). The display of screen B may occur immediately after the appropriate access control 66*b* is activated, or there may be one or more intermediate controls/screens that need to be followed before getting to screen B. However arrived at, the display of screen B includes an auxiliary disarm control 66*d* that, when activated, causes exit detection system 56 to be disarmed. Auxiliary disarm control 66*d*, in this embodiment, is one of the touchscreen controls 66*b*. In other embodiments, auxiliary disarm control 66*d* can be implemented as one or more non-touchscreen controls 66*c*.

Regardless of whether implemented as a touchscreen control 66*b* or a non-touchscreen control 66*c*, or a combination thereof, auxiliary disarm control 66*d*, as explained previously, is not disabled when a patient moves within a disablement zone 86. This allows a caregiver, or other authorized individual, who knows how to bring up screen B on display 64 to disarm exit detection system 56 even when the patient is positioned within a disablement zone 86. This can be useful in situations where a caregiver responds to an exit alert and finds the patient seated, or otherwise positioned in, a disablement zone 86 and the caregiver does not wish to wait until the patient is moved out of the disablement zone 86 before disarming exit detection system 56.

It will be understood by those skilled in the art that screen A of FIG. 11 is merely a generic screen that may vary with time and/or user manipulation. No matter how screen A is configured in a particular embodiment or at a particular moment, it is displayed by controller 58 in a manner that does not include auxiliary disarm control 66*d*. In some instances, a user may need to press other controls 66 in order to first get to screen A, and then use the access control 66*b* to get to screen B and auxiliary disarm control 66*d*. Controller 58 may therefore be programmed to display any type of content on screen A other than content that shows auxiliary disarm control 66*d*. Controller 58 may further be programmed to start displaying screen A automatically in response to either an exit alert being issued and/or the patient moving into a disablement zone 86.

It will be understood by those skilled in the art that the disarm control 66*a* referred to herein may take on a variety of different forms. In some embodiments, disarm control 66*a* may function to permanently disarm exit detection system 56 until a caregiver re-arms the exit detection system. In other embodiments, disarm control 66*a* is alternatively implemented as a "pause" or "suspend" control that pauses the exit detection system 56 for some amount of time (which may be fixed or variable), such as, but not limited to, until the occurrence of a specific event. In still other embodiments, disarm control 66*a* is a mute control that merely silences any audible sounds being created by alarm 60 (or a remote alarm) for a period of time. Such a muting function may also involve pausing any visual alerting that alarm 60 (or a remote alarm) is engaged in as a part of the exit alerting function.

It will also be understood that, although exit detection system 56 has been primarily described herein as using the patient's center of gravity to determine when to issue an exit alert and when to disable disarm control 66*a*, controller 58 may be programmed to utilize the outputs of load cells 54 in other manners for one or both of these determinations (exit alerting and disarm control disablement). One such alternative manner involves summing total amount of force on load cells 54 when patient support apparatus 20 is occupied and then looking for shifts of more than a threshold amount of that weight to a side, head end, or foot end of patient support apparatus. For example, if a 100 kilogram person is occupying patient support apparatus 20, exit detection system 56 may be modified to trigger an exit alert and/or disable disarm control 66*a* if more than X percent, say, 70 percent (0.70×100=70 kilograms) of the total forces are detected by the two load cells 54 positioned along the foot end 38 of patient support apparatus 20. Other ratios may be used for the sides of patient support apparatus and/or the head end of patient support apparatus. Exit detection system 56 can therefore be modified to compute one or more ratios of the force detected by one or more of the load cells 54 to determine when to issue an exit alert and/or when to disable disarm control 66*a*.

Still other variations of exit detection system 56 may be implemented in other embodiments. For example, in some alternative embodiments, exit detection system 56 alternatively, or additionally, uses a pressure sensing mat positioned on top of support deck 30 that detects the interface pressures exerted by the patient while supported on patient support apparatus 20. The outputs from the pressures sensing mat, which indicate not only the magnitude of the patient interface pressure values, but also the location of the interface values on the pressure sensing mat, are fed to a controller, such as controller 58, and used to determine the patient's position. If a center of pressure of the patient, or some other indicator of the patient's location, moves to less than the threshold distance 84 away from the disarm control 66*a*, as detected by the sensing mat, controller 58 disables the disarm control 66*a*, or otherwise acts in the manners disclosed herein (e.g. follows exit alerting algorithm 190). One such suitable pressure sensing mat that may be incorporated into exit detection system 56 is disclosed in commonly assigned U.S. patent publication 2014/0039351 filed Mar. 2, 2012, by inventors Joshua Mix et al. and entitled SENSING SYSTEM FOR PATIENT SUPPORTS, the complete disclosure of which is hereby incorporated herein by reference.

In other alternative embodiments, exit detection system 56 is implemented by analyzing patient movement from video or thermal images of the patient captured by one or more cameras positioned and aimed to include the patient in their field of view. Examples of suitable thermal and video camera systems that can be used for this purpose are disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, and commonly assigned U.S. patent application Ser. No. 14/578,630 filed Dec. 22, 2014, by inventors Richard Derenne et al. and entitled VIDEO MONITORING SYSTEM, the complete disclosures of both of which are hereby incorporated herein by reference. Still other types of imaging systems for detecting patient movement toward disarm control 66*a* may be used.

In still other embodiments, exit detection system 56 may be implemented to include one or more sensors that detect the patient's orientation and/or body part positions while positioned on patient support apparatus 20. Such sensors may be in addition to, or in lieu of, any of the previously mentioned sensors of exit detection system 56. The body orientation/position sensors are used to disable disarm control 66*a* when the patient reaches toward disarm control 66*a* and/or otherwise acts in a manner that suggests the patient is trying to disarm exit detection system 56. One manner in which controller 58 may determine the orientation of the occupant's body is disclosed in commonly assigned U.S. patent application Ser. No. 14/873,734 filed Oct. 2, 2015, by inventors Marko Kostic et al. and entitled PERSON SUPPORT APPARATUS WITH MOTION MONITORING, the complete disclosure of which is incorporated herein by reference. Other manners are disclosed in commonly assigned U.S. patent application Ser. No. 15/346,779 filed Nov. 9, 2016, by inventors Marko Kostic et al. and entitled PATIENT SUPPORT APPARATUSES WITH ACCELERATION DETECTION, which is also incorporated herein by reference in its entirety. Still other manners of determining the occupant's orientation and/or body part positions may also be used.

In still other embodiments, exit detection system 56 may be implemented to monitor the amount of kinetic energy of the patient and to issue an exit alert if the kinetic energy, momentum, or other velocity-dependent parameter exceeds a threshold. The threshold may be variable based on a direction of the kinetic energy, momentum, or other velocity-based parameter. Still further, the threshold may vary based on the position (up/down) of one or more siderails of the patient support apparatus. In any of these embodiments, controller 58 may utilize the kinetic energy, momentum, or other velocity-dependent parameter to decide whether to disable the disarm control 66*a*, or otherwise act in the manners disclosed herein (e.g. following exit alerting algorithm 190).

It will be understood by those skilled in the art that the disablement features of exit alerting algorithms 90 and 190 discussed above may be applied to other functions and/or controls of patient support apparatus 20 in addition to, or in lieu of, the disarm control 66*a*. That is, in some embodiments, patient support apparatus 20 is configured to disable one or more other controls when a patient's movement indicates that he or she may be attempting to disable a caregiver-implemented setting on the patient support apparatus 20. For example, patient support apparatus 20 may include one or more lockout controls (not shown) that, when activated, prevent a patient from pivoting the Fowler section (head section 40), from raising and/or lowering litter frame 28, and/or from moving other portions of support deck 30. In some of such embodiments, patient support apparatus 20 is configured to disable the disarming of one or more of these lockout controls when the patient moves toward the lockout controls, thereby helping to prevent the patient from changing a caregiver-implemented control. Additional examples of these kinds of patient support apparatuses are discussed below.

In at least one embodiment, patient support apparatus 20 includes a conventional lockout that prevents head section 40 (i.e. the Fowler section) from being pivoted lower than a specific angular orientation. In other words, it partially locks out movement of the Fowler section. This partial Fowler section lockout is typically used by caregiver in order to help prevent ventilator associated pneumonia. In order to activate this partial Fowler lockout, the caregiver activates a lockout control on one of the user interfaces, such as, but not limited to, footboard user interface 48*a*. The user interface 48 also includes a control for deactivating the partial Fowler lockout which, in some cases, may be the same control used to activate the partial Fowler lockout (e.g. a toggle switch that alternately activates and deactivates the lockout control). In such embodiments, controller 58 is configured to disable the partial Fowler lockout deactivation control when the patient moves toward the deactivation control, thereby preventing the patient from changing the caregiver-implemented lockout.

In yet another embodiment, patient support apparatus 20 includes a lockout alert function that issues an alert if the partial Fowler lockout is deactivated. One example of such a partial Fowler lockout alert is disclosed in commonly assigned U.S. Pat. No. 8,844,076 issued to Becker et al. on Sep. 30, 2014, and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is incorporated herein by reference. In this embodiment, controller 58 is configured to temporarily disable the control for deactivating the partial Fowler lockout alert when the patient moves toward this control in any of the manners cited above. This helps prevent the patient from secretly deactivating the Fowler lockout function by ensuring that a corresponding alert is sent to the caregiver anytime the Fowler lockout function is deactivated (unless it is deactivated by the caregiver when the patient has not moved outside of the permitted movement zone 80, or otherwise moved in a manner causing controller 58 to disable this alert function).

In another embodiment of patient support apparatus 20, one or more of the user interfaces 48 includes a caregiver control that, when activated, causes the patient support apparatus 20 to issue an alert when one or more of the siderails 34 are lowered, or otherwise changed from a desired position. In such embodiments, controller 58 is configured to prevent the patient from deactivating this caregiver control by disabling the corresponding deactivation control whenever the patient moves closer than a threshold distance to the deactivation control.

In still other embodiments, patient support apparatus 20 includes a control for activating a bed monitoring feature that, when activated, instructs controller 58 to monitor a plurality of settings and to issue an alert when any one or more of the plurality of settings changes to an undesired state. Examples of a patient support apparatus having such a bed monitoring feature are disclosed in commonly assigned U.S. patent publication 2015/0000035 filed Sep. 17, 2014, by inventors David Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is incorporated herein by reference. In that publication, the patient support apparatus includes a bed status button 84 that, when pressed, monitors a plurality of settings (e.g. a brake, siderails, exit detection system, etc.) of the patient support apparatus 20 and issues an alarm if any one or more of the conditions change to an undesired state. The bed status button 84 is a toggle button such that, when pressed again, the monitoring of the plurality of settings changes. In at least one embodiment of a patient support apparatus 20 according to the present disclosure, patient support apparatus 20 includes a control, such as, but not limited to, a control like the bed status button 84 of the '035 publication that is disabled from being deactivated when a patient moves within a threshold distance of the control.

In other embodiments, patient support apparatus 20 includes one or more controls for activating and deactivating a brake of the patient support apparatus. Controller 58 is configured in such embodiments to disable the control for deactivating the brake if the patient moves within a threshold distance of any of the brake deactivation controls.

In still other embodiments, patient support apparatus 20 includes a power control for turning electrical power off to the patient support apparatus (in some embodiments, the power control may be a toggle button or switch that alternates between turning power on and off to the patient support apparatus). Controller 58 is configured in such embodiments to disable the power control such that the patient cannot shut off power to the patient support apparatus when the patient moves within a threshold distance of the power control.

In still other embodiments, patient support apparatus 20 is constructed to include a propulsion system that drives one or more wheels of the patient support apparatus 20 in order to reduce the amount of effort a caregiver needs to push the patient support apparatus 20 to different locations. One example of such a propulsion system is disclosed in commonly assigned U.S. patent application Ser. No. 15/189,149 filed Jun. 22, 2016, by inventors Jerald Trepanier et al. and entitled PERSON SUPPORT APPARATUSES WITH DRIVE CONTROLS, the complete disclosure of which is incorporated herein by reference. Such propulsion systems typically include one or more controls at the head or foot end of the patient support apparatus 20 for driving and/or steering the patient support apparatus 20. In such embodiments, controller 58 may be configured to disable one or more of the propulsion controls (e.g. driving and/or steering controls) when the patient has moved within a threshold distance of such controls.

Controller 58 may be configured to disable the deactivation control of still other types of caregiver settings of patient support apparatus 20 when a patient moves within a threshold distance of the deactivation control, in still other embodiments.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:

a frame;

a support surface configured to support a patient thereon;

an exit detection system adapted to be in an armed state or a disarmed state, the exit detection system comprising a plurality of exit detection sensors configured to detect when a patient exits from the support surface and a controller configured to issue an exit alert when the patient exits from the support surface and the exit detection system is in the armed state; and a control configured to disarm the exit detection system while the exit detection is in the armed state;

wherein the controller is configured, while the exit detection system is in the armed state, to perform the following:

use outputs from the exit detection sensors to detect a first patient movement indicating an attempt by the patient to disarm the exit detection system, use outputs from the exit detection sensors to detect a second patient movement not indicating an attempt by the patient to disarm the exit detection system, disable the control in response to detecting the first patient movement, and not disable the control in response to detecting the second patient movement.

2. The patient support apparatus of claim 1 wherein the exit detection sensors comprise a plurality of load cells configured to detect downward forces exerted on the support surface by the patient.

3. The patient support apparatus of claim 2 wherein the controller is configured to use outputs from the plurality of load cells to compute a center of gravity of the patient, and the controller is further configured to use the center of gravity of the patient to detect the first and second patient movement.

4. The patient support apparatus of claim 3 wherein the control is positioned at a foot end of the patient support apparatus and the controller is configured to detect the first patient movement in response to a distance between the patient's center of gravity and a foot end of the patient support apparatus decreasing below a threshold.

5. The patient support apparatus of claim 4 wherein the controller is further configured to use outputs from the exit detection sensors to detect when the first patient movement ceases and to enable the control in response to cessation of the first patient movement.

6. The patient support apparatus of claim 3 further comprising:

a base;

a lift subsystem configured to raise and lower the support surface with respect to the base;

a plurality of siderails moveable between raised and lowered positions; and a control panel positioned on an outside surface of at least one of the siderails, the control panel including the control.

7. A patient support apparatus comprising:

a frame;

a support surface configured to support a patient thereon;

an exit detection system adapted to be in an armed state and a disarmed state, the exit detection system comprising a controller and a plurality of exit detection sensors configured to detect a patient's position relative to a boundary condition and a distance of the patient from a user interface, the controller configured to issue an exit alert when the patient's position crosses the boundary condition and the exit detection system is in the armed state; and a control configured to disarm the exit detection system while the exit detection system is in the armed state, the control coupled to the user interface;

wherein the controller is configured to disable the control in response to the distance of the patient from the user interface decreasing below a threshold while the exit detection system is in the armed state, and to not disable the control in response to the distance of the patient from the user interface not decreasing below the threshold while the exit detection system is armed.

8. The patient support apparatus of claim 7 wherein the exit detection sensors comprise a plurality of load cells configured to detect downward forces exerted on the support surface by the patient.

9. The patient support apparatus of claim 8 wherein the controller is further configured to use outputs from the plurality of load cells to compute a center of gravity of the patient and to use the center of gravity to both detect when the patient's position crosses the boundary condition and when the distance of the patient from the user interface decreases below the threshold.

10. The patient support apparatus of claim 9 wherein the controller is configured to disable the control for a predetermined minimum amount of time after the distance of the patient from the user interface decreases below the threshold.

11. The patient support apparatus of claim 9 further comprising a second control configured to disarm the exit detection system, the second control coupled to a second user interface spaced from the user interface, and wherein the controller is further configured to detect a second distance of the patient from the second user interface and the controller is configured to disable the second control in response to the second distance decreasing below a second threshold while the exit detection system is armed.

12. The patient support apparatus of claim 11 wherein the threshold and the second threshold are defined such that the patient is able to move to a first location on the support surface where the distance is below the threshold but the second distance is not below the second threshold, and the patient is also able to move to a second location on the support surface where the distance is not below the threshold but the second distance is below the second threshold.

13. A patient support apparatus comprising:

a frame;

a support surface configured to support a patient thereon;

an exit detection system adapted to be in an armed state or a disarmed state, the exit detection system comprising a controller and a plurality of exit detection sensors configured to detect a patient's position relative to a boundary condition and a distance of the patient from a user interface, the controller configured to issue an exit alert when the patient's position crosses the boundary condition and the exit detection system is in the armed state; and a control configured to disarm the exit detection system when the control is activated and the exit detection system is in the armed state, the control coupled to the user interface;

wherein the controller is configured to issue the exit alert for a first time period in response to the patient's position crossing the boundary condition and the distance of the patient from the user interface decreasing below a threshold, to issue the exit alert for a second time period in response to the patient's position crossing the boundary condition and the distance of the patient from the user interface not decreasing below the threshold, and to maintain an aural component of the exit alert for all of the first time period regardless of a user activating the control, the first time period being different from the second time period.

14. The patient support apparatus of claim 13 wherein the first time period is defined to include a minimum amount of time and the second time period does not include a minimum amount of time.

15. The patient support apparatus of claim 14 wherein the second time period is a variable amount of time, and the variable amount of time ends when an event occurs.

16. The patient support apparatus of claim 15 wherein the event includes at least one of the following: (a) a user activating the control to disarm the exit detection system; or (b) the patient's position moving back across the boundary condition.

17. The patient support apparatus of claim 13 wherein the first time period is a fixed amount of time and the second time period is a variable amount of time.

18. The patient support apparatus of claim 13 wherein the exit detection sensors comprise a plurality of load cells configured to detect downward forces exerted on the support surface by the patient.

19. The patient support apparatus of claim 18 wherein the controller is configured to use outputs from the plurality of load cells to compute a center of gravity of the patient and to use the center of gravity to both detect when the patient's position crosses the boundary condition and when the distance of the patient from the user interface decreases below the threshold.

20. The patient support apparatus of claim 19 wherein the controller is further configured to disable the control in response to the distance of the patient from the user interface decreasing below the threshold while the exit detection system is armed.

* * * * *